US010058681B2

(12) United States Patent
Skakoon et al.

(10) Patent No.: US 10,058,681 B2
(45) Date of Patent: Aug. 28, 2018

(54) LOW PROFILE INSTRUMENT IMMOBILIZER

(71) Applicant: Medtronic, Inc., Minneapolis, MN (US)

(72) Inventors: James G. Skakoon, St. Paul, MN (US); Matthew S. Solar, Indialantic, FL (US); Thomas I. Miller, Palm Bay, FL (US); Patrick R. Helmer, Melbourne, FL (US); Mark S. Freas, Palm Bay, FL (US)

(73) Assignee: Medtronic, Inc., Minneapolis, MN (US)

( * ) Notice: Subject to any disclaimer, the term of this patent is extended or adjusted under 35 U.S.C. 154(b) by 417 days.

(21) Appl. No.: 13/828,136

(22) Filed: Mar. 14, 2013

(65) Prior Publication Data

US 2013/0197472 A1     Aug. 1, 2013

Related U.S. Application Data

(60) Continuation of application No. 12/730,724, filed on Mar. 24, 2010, now Pat. No. 9,901,713, which is a
(Continued)

(51) Int. Cl.
*A61M 25/02* (2006.01)
*A61B 5/00* (2006.01)
(Continued)

(52) U.S. Cl.
CPC ........... *A61M 25/02* (2013.01); *A61B 5/6864* (2013.01); *A61B 17/3423* (2013.01);
(Continued)

(58) Field of Classification Search
CPC ............ A61B 17/3415; A61B 17/3423; A61B 2017/347; A61B 19/26; A61B 19/201; A61M 25/02; A61M 2025/024
(Continued)

(56) References Cited

U.S. PATENT DOCUMENTS

| 431,187 A | 7/1890 | Foster |
| 438,801 A | 10/1890 | Delehanty |

(Continued)

FOREIGN PATENT DOCUMENTS

| CA | 2405224 A1 | 10/2001 |
| DE | 3108766 | 9/1982 |

(Continued)

OTHER PUBLICATIONS

"Cross-Hairs Kit", Elekta Instruction for Use Brochure, pp. 2-5.
(Continued)

*Primary Examiner* — Diane Yabut
(74) *Attorney, Agent, or Firm* — Harness, Dickey & Pierce, P.L.C.

(57) ABSTRACT

This document discusses, among other things, examples of a low profile instrument immobilizer and means for positioning the same. In one example, the low profile instrument immobilizer grasps, secures, and immobilizes an electrode or other instrument that extends through a burr hole in a skull to a target location in a patient's brain.

37 Claims, 30 Drawing Sheets

Related U.S. Application Data division of application No. 11/005,907, filed on Dec. 6, 2004, now Pat. No. 7,704,260, which is a continuation-in-part of application No. PCT/US03/28966, filed on Sep. 17, 2003.

(60) Provisional application No. 60/411,309, filed on Sep. 17, 2002.

(51) Int. Cl.
*A61B 90/50* (2016.01)
*A61B 90/11* (2016.01)
*A61B 17/34* (2006.01)
*A61N 1/05* (2006.01)
*A61B 90/10* (2016.01)

(52) U.S. Cl.
CPC ............ *A61B 90/11* (2016.02); *A61B 90/50* (2016.02); *A61N 1/0539* (2013.01); *A61B 17/3415* (2013.01); *A61B 2017/347* (2013.01); *A61B 2090/103* (2016.02); *A61M 2025/024* (2013.01); *A61N 1/0536* (2013.01)

(58) Field of Classification Search
USPC ......... 606/129, 130; 604/174, 178; 607/115, 607/116
See application file for complete search history.

(56) References Cited

U.S. PATENT DOCUMENTS

| | | |
|---|---|---|
| 873,009 A | 12/1907 | Baxter |
| 1,129,333 A | 2/1915 | Clarke |
| 1,664,210 A | 3/1928 | Hall |
| 2,119,649 A | 6/1938 | Roosen |
| 2,135,160 A | 11/1938 | Beekhuis |
| 2,497,820 A | 2/1950 | Kielland |
| 2,659,371 A * | 11/1953 | Schnee ................... 606/157 |
| 2,686,890 A | 8/1954 | Davis |
| 3,010,347 A | 11/1961 | Kron |
| 3,016,899 A | 1/1962 | Stenvall |
| 3,017,887 A | 1/1962 | Heyer |
| 3,055,370 A | 9/1962 | McKinney et al. |
| 3,055,371 A | 9/1962 | Kulick et al. |
| 3,115,140 A | 12/1963 | Volkman |
| 3,135,263 A | 6/1964 | Connelley, Jr. |
| 3,223,087 A | 12/1965 | Vladyka et al. |
| 3,262,452 A | 7/1966 | Hardy et al. |
| 3,273,559 A | 9/1966 | Evans |
| 3,282,152 A | 11/1966 | Myer |
| 3,402,710 A | 9/1968 | Paleschuck |
| 3,444,861 A | 5/1969 | Schulte |
| 3,457,922 A | 7/1969 | Ray |
| 3,460,537 A | 8/1969 | Zeis |
| 3,508,552 A | 4/1970 | Hainault |
| 3,672,352 A | 6/1972 | Summers |
| 3,760,811 A | 9/1973 | Andrew |
| 3,783,873 A | 1/1974 | Jacobs |
| 3,817,249 A | 6/1974 | Nicholson |
| 3,893,449 A | 7/1975 | Lee et al. |
| 3,981,079 A | 9/1976 | Lenczycki |
| 4,013,080 A | 3/1977 | Froning |
| 4,025,964 A | 5/1977 | Owens |
| 4,026,276 A | 5/1977 | Chubbuck |
| 4,040,427 A | 8/1977 | Winnie |
| 4,131,257 A | 12/1978 | Sterling |
| 4,230,117 A | 10/1980 | Anichkov et al. |
| 4,265,252 A | 5/1981 | Chubbuck et al. |
| 4,278,042 A | 7/1981 | Lindquist |
| 4,312,337 A | 1/1982 | Donohue |
| 4,318,401 A | 3/1982 | Zimmerman |
| 4,328,813 A | 5/1982 | Ray |
| 4,341,220 A | 7/1982 | Perry |
| 4,345,606 A | 8/1982 | Littleford |
| 4,350,159 A | 9/1982 | Gouda |
| 4,355,645 A | 10/1982 | Mitani et al. |
| 4,360,025 A | 11/1982 | Edwards |
| 4,386,602 A | 6/1983 | Sheldon et al. |
| 4,418,894 A | 12/1983 | Mailliet et al. |
| 4,448,195 A | 5/1984 | LeVeen et al. |
| 4,463,758 A | 8/1984 | Patil et al. |
| 4,475,550 A | 10/1984 | Bremer et al. |
| 4,483,344 A | 11/1984 | Atkov et al. |
| 4,571,750 A | 2/1986 | Barry |
| 4,572,198 A | 2/1986 | Codrington |
| 4,579,120 A | 4/1986 | MacGregor |
| 4,592,352 A | 6/1986 | Patil |
| 4,598,708 A | 7/1986 | Beranek |
| 4,608,977 A | 9/1986 | Brown |
| 4,617,925 A | 10/1986 | Laitinen |
| 4,618,978 A | 10/1986 | Cosman |
| 4,629,451 A | 12/1986 | Winters et al. |
| 4,638,798 A | 1/1987 | Shelden et al. |
| 4,638,804 A | 1/1987 | Jewusiak |
| 4,660,563 A | 4/1987 | Lees |
| 4,665,928 A | 5/1987 | Linial et al. |
| 4,699,616 A | 10/1987 | Nowak et al. |
| 4,705,436 A | 11/1987 | Robertson et al. |
| 4,706,665 A | 11/1987 | Gouda |
| 4,733,661 A | 3/1988 | Palestrant |
| 4,755,642 A | 7/1988 | Parks |
| 4,791,934 A | 12/1988 | Brunnett |
| 4,793,355 A | 12/1988 | Crum et al. |
| 4,798,208 A | 1/1989 | Faasse, Jr. |
| 4,805,615 A | 2/1989 | Carol |
| 4,805,634 A | 2/1989 | Ullrich et al. |
| 4,807,620 A | 2/1989 | Strul et al. |
| 4,809,694 A | 3/1989 | Ferrara |
| 4,824,436 A | 4/1989 | Wolinsky |
| 4,826,487 A | 5/1989 | Winter |
| 4,869,247 A | 9/1989 | Howard, III et al. |
| 4,883,053 A | 11/1989 | Simon |
| 4,896,673 A | 1/1990 | Rose et al. |
| 4,902,129 A | 2/1990 | Siegmund et al. |
| 4,922,924 A | 5/1990 | Gambale et al. |
| 4,955,891 A | 9/1990 | Carol |
| 4,957,481 A | 9/1990 | Gatenby |
| 4,986,280 A | 1/1991 | Marcus et al. |
| 4,986,281 A | 1/1991 | Preves et al. |
| 4,989,608 A | 2/1991 | Ratner |
| 4,991,579 A | 2/1991 | Allen |
| 4,993,425 A | 2/1991 | Kronberg |
| 4,998,938 A | 3/1991 | Ghajar et al. |
| 5,006,122 A | 4/1991 | Wyatt et al. |
| 5,024,236 A | 6/1991 | Shapiro |
| 5,027,818 A | 7/1991 | Bova et al. |
| 5,030,223 A | 7/1991 | Anderson et al. |
| 5,050,608 A | 9/1991 | Watanabe et al. |
| 5,052,329 A | 10/1991 | Bennett |
| 5,054,497 A | 10/1991 | Kapp et al. |
| 5,057,084 A | 10/1991 | Ensminger et al. |
| 5,057,106 A | 10/1991 | Kasevich et al. |
| 5,065,761 A | 11/1991 | Pell |
| 5,078,140 A | 1/1992 | Kwoh |
| 5,078,142 A | 1/1992 | Siczek et al. |
| 5,080,662 A | 1/1992 | Paul |
| 5,087,256 A | 2/1992 | Taylor et al. |
| 5,099,846 A | 3/1992 | Hardy |
| 5,102,402 A | 4/1992 | Dror et al. |
| 5,116,344 A | 5/1992 | Sundqvist et al. |
| 5,116,345 A | 5/1992 | Jewell et al. |
| 5,120,322 A | 6/1992 | Davis et al. |
| 5,125,888 A | 6/1992 | Howard et al. |
| 5,142,930 A | 9/1992 | Allen et al. |
| 5,143,086 A | 9/1992 | Duret et al. |
| 5,154,179 A | 10/1992 | Ratner |
| 5,154,723 A | 10/1992 | Kubota et al. |
| 5,163,430 A | 11/1992 | Carol |
| 5,166,875 A | 11/1992 | Machida et al. |
| 5,171,217 A | 12/1992 | March et al. |
| 5,174,297 A | 12/1992 | Daikuzono et al. |
| 5,186,174 A | 2/1993 | Schlondorff et al. |
| 5,201,742 A | 4/1993 | Hasson |

(56) References Cited

U.S. PATENT DOCUMENTS

| | | |
|---|---|---|
| 5,207,223 A | 5/1993 | Adler |
| 5,207,688 A | 5/1993 | Carol |
| 5,211,165 A | 5/1993 | Dumoulin et al. |
| 5,221,264 A | 6/1993 | Wilk et al. |
| 5,222,499 A | 6/1993 | Allen et al. |
| 5,230,338 A | 7/1993 | Allen et al. |
| 5,230,623 A | 7/1993 | Guthrie et al. |
| 5,242,415 A | 9/1993 | Kantrowitz et al. |
| 5,246,448 A | 9/1993 | Chang |
| 5,257,998 A | 11/1993 | Ota et al. |
| 5,263,939 A | 11/1993 | Wortrich |
| 5,263,956 A | 11/1993 | Nobles |
| 5,267,970 A | 12/1993 | Chin et al. |
| 5,269,305 A | 12/1993 | Corol |
| 5,279,309 A | 1/1994 | Taylor et al. |
| 5,279,575 A | 1/1994 | Sugarbaker |
| 5,280,427 A | 1/1994 | Magnusson et al. |
| 5,290,266 A | 3/1994 | Rohling et al. |
| 5,291,890 A | 3/1994 | Cline et al. |
| 5,300,080 A | 4/1994 | Clayman et al. |
| 5,305,203 A | 4/1994 | Raab |
| 5,306,272 A | 4/1994 | Cohen et al. |
| 5,309,913 A | 5/1994 | Kormos et al. |
| 5,330,485 A | 7/1994 | Clayman et al. |
| 5,354,283 A | 10/1994 | Bark et al. |
| 5,360,020 A | 11/1994 | Lee, Sr. et al. |
| 5,361,763 A | 11/1994 | Kao et al. |
| 5,366,446 A | 11/1994 | Tal et al. |
| 5,375,588 A | 12/1994 | Yoon |
| 5,375,596 A | 12/1994 | Twiss et al. |
| 5,380,302 A | 1/1995 | Orth |
| 5,383,454 A | 1/1995 | Bucholz |
| 5,387,220 A | 2/1995 | Pisharodi |
| 5,394,457 A | 2/1995 | Leibinger et al. |
| 5,405,330 A | 4/1995 | Zunitch et al. |
| 5,423,832 A | 6/1995 | Gildenberg |
| 5,423,848 A | 6/1995 | Washizuka et al. |
| 5,445,166 A | 8/1995 | Taylor |
| 5,452,720 A | 9/1995 | Smith et al. |
| 5,462,555 A | 10/1995 | Bolanos et al. |
| 5,464,446 A | 11/1995 | Dreessen et al. |
| 5,470,307 A | 11/1995 | Lindall |
| 5,474,564 A | 12/1995 | Clayman et al. |
| 5,483,961 A | 1/1996 | Kelly et al. |
| 5,494,034 A | 2/1996 | Schlondorff et al. |
| 5,494,655 A | 2/1996 | Rocklage et al. |
| 5,515,160 A | 5/1996 | Schulz et al. |
| 5,517,990 A | 5/1996 | Kalfas et al. |
| 5,528,652 A | 6/1996 | Smith et al. |
| 5,541,377 A | 7/1996 | Stuhlmacher |
| 5,572,905 A | 11/1996 | Cook, Jr. |
| 5,572,999 A | 11/1996 | Funda et al. |
| 5,575,798 A | 11/1996 | Koutrouvelis |
| 5,608,382 A | 3/1997 | Webb et al. |
| 5,618,288 A | 4/1997 | Calvo et al. |
| 5,622,170 A | 4/1997 | Schulz |
| 5,638,819 A | 6/1997 | Manwaring et al. |
| 5,639,276 A | 6/1997 | Weinstock et al. |
| 5,643,286 A | 7/1997 | Warner et al. |
| 5,647,361 A | 7/1997 | Damadian |
| 5,649,936 A | 7/1997 | Real |
| 5,658,272 A | 8/1997 | Hasson |
| 5,662,600 A | 9/1997 | Watson et al. |
| 5,667,514 A | 9/1997 | Heller |
| 5,695,501 A | 12/1997 | Carol et al. |
| 5,713,858 A | 2/1998 | Heruth et al. |
| 5,755,697 A | 5/1998 | Jones et al. |
| 5,776,064 A | 7/1998 | Kalfas et al. |
| 5,776,143 A | 7/1998 | Adams et al. |
| 5,776,144 A | 7/1998 | Leysieffer et al. |
| 5,788,713 A | 8/1998 | Dubach et al. |
| 5,807,033 A | 9/1998 | Benway |
| 5,809,694 A | 9/1998 | Postans et al. |
| 5,810,712 A | 9/1998 | Dunn |
| 5,817,106 A | 10/1998 | Real |
| 5,817,116 A | 10/1998 | Takahashi et al. |
| 5,823,975 A | 10/1998 | Stark et al. |
| 5,833,627 A | 11/1998 | Shmulewitz et al. |
| 5,843,150 A | 12/1998 | Dreessen et al. |
| 5,851,183 A | 12/1998 | Bucholz |
| 5,865,817 A | 2/1999 | Moenning et al. |
| 5,865,842 A | 2/1999 | Knuth et al. |
| 5,871,445 A | 2/1999 | Bucholz |
| 5,871,487 A | 2/1999 | Warner et al. |
| 5,873,822 A | 2/1999 | Ferre et al. |
| 5,891,034 A | 4/1999 | Bucholz |
| 5,891,157 A | 4/1999 | Day et al. |
| 5,916,200 A | 6/1999 | Eppley et al. |
| 5,927,277 A * | 7/1999 | Baudino et al. .............. 600/386 |
| 5,950,629 A | 9/1999 | Taylor et al. |
| 5,954,687 A | 9/1999 | Baudino |
| 5,957,933 A | 9/1999 | Yanof et al. |
| 5,957,934 A | 9/1999 | Rapoport et al. |
| 5,964,705 A | 10/1999 | Truwit et al. |
| 5,980,535 A | 11/1999 | Barnett et al. |
| 5,984,930 A | 11/1999 | Maciunas et al. |
| 5,993,463 A | 11/1999 | Truwit |
| 5,997,471 A | 12/1999 | Gumb et al. |
| 6,004,304 A | 12/1999 | Suzuki et al. |
| 6,006,126 A | 12/1999 | Cosman |
| 6,018,094 A | 1/2000 | Fox |
| 6,021,343 A | 2/2000 | Foley et al. |
| 6,024,729 A | 2/2000 | Dehdashtian et al. |
| 6,030,223 A | 2/2000 | Sugimori |
| 6,039,725 A | 3/2000 | Moenning et al. |
| 6,042,540 A | 3/2000 | Johnston et al. |
| 6,044,304 A | 3/2000 | Baudino |
| 6,058,323 A | 5/2000 | Lemelson |
| 6,071,288 A | 6/2000 | Carol et al. |
| 6,076,008 A | 6/2000 | Bucholz |
| 6,079,681 A | 6/2000 | Stern et al. |
| 6,110,182 A | 8/2000 | Mowlai-Ashtiani |
| 6,117,143 A | 9/2000 | Hynes et al. |
| 6,120,465 A | 9/2000 | Guthrie et al. |
| 6,134,477 A | 10/2000 | Knuteson |
| 6,135,946 A | 10/2000 | Konen et al. |
| 6,179,826 B1 | 1/2001 | Aebischer et al. |
| 6,195,577 B1 | 2/2001 | Truwit et al. |
| 6,206,890 B1 | 3/2001 | Truwit |
| 6,210,417 B1 | 4/2001 | Baudino et al. |
| 6,231,526 B1 | 5/2001 | Taylor et al. |
| 6,236,875 B1 | 5/2001 | Bucholz et al. |
| 6,238,402 B1 | 5/2001 | Sullivan, III et al. |
| 6,254,532 B1 | 7/2001 | Paolitto et al. |
| 6,257,407 B1 | 7/2001 | Truwit et al. |
| 6,261,300 B1 | 7/2001 | Carol et al. |
| 6,267,769 B1 | 7/2001 | Truwit |
| 6,267,770 B1 | 7/2001 | Truwit |
| 6,273,896 B1 | 8/2001 | Franck et al. |
| 6,282,437 B1 | 8/2001 | Franck et al. |
| 6,290,644 B1 | 9/2001 | Green, II et al. |
| 6,298,262 B1 | 10/2001 | Franck et al. |
| 6,315,770 B1 | 11/2001 | de la Torre et al. |
| 6,321,104 B1 | 11/2001 | Gielen et al. |
| 6,324,433 B1 | 11/2001 | Errico |
| 6,327,491 B1 | 12/2001 | Franklin et al. |
| 6,356,792 B1 | 3/2002 | Errico et al. |
| 6,368,329 B1 | 4/2002 | Truwit |
| 6,400,992 B1 | 6/2002 | Borgersen et al. |
| 6,457,963 B1 | 10/2002 | Tawara et al. |
| 6,482,182 B1 | 11/2002 | Carroll et al. |
| 6,488,620 B1 | 12/2002 | Segermark et al. |
| 6,491,699 B1 | 12/2002 | Henderson et al. |
| 6,529,765 B1 | 3/2003 | Franck et al. |
| 6,537,232 B1 | 3/2003 | Kucharczyk et al. |
| 6,546,277 B1 | 4/2003 | Franck et al. |
| 6,546,279 B1 | 4/2003 | Bova et al. |
| 6,547,795 B2 | 4/2003 | Schneiderman |
| 6,554,802 B1 | 4/2003 | Pearson et al. |
| 6,556,857 B1 | 4/2003 | Estes et al. |
| 6,609,020 B2 | 8/2003 | Gill et al. |
| 6,610,100 B2 | 8/2003 | Phelps et al. |
| 6,623,490 B1 | 9/2003 | Crane et al. |
| 6,632,184 B1 | 10/2003 | Truwit |

(56) References Cited

U.S. PATENT DOCUMENTS

| | | |
|---|---|---|
| 6,655,014 B1 | 12/2003 | Babini |
| 6,662,035 B2 | 12/2003 | Sochor |
| 6,676,669 B2 | 1/2004 | Charles et al. |
| 6,682,538 B2 | 1/2004 | Qiu et al. |
| 6,706,050 B1 | 3/2004 | Giannadakis |
| 6,726,678 B1 | 4/2004 | Nelson et al. |
| 6,746,471 B2 | 6/2004 | Mortier et al. |
| 6,752,812 B1 | 6/2004 | Truwit |
| 6,765,122 B1 | 7/2004 | Stout |
| 6,773,443 B2 | 8/2004 | Truwit et al. |
| 6,782,288 B2 | 8/2004 | Truwit et al. |
| 6,802,323 B1 | 10/2004 | Truwit et al. |
| 6,817,995 B1 | 11/2004 | Halpern |
| 6,902,569 B2 | 6/2005 | Parmer et al. |
| 6,913,478 B2 | 7/2005 | Lamirey et al. |
| 6,944,895 B2 | 9/2005 | Truwit |
| 6,960,216 B2 | 11/2005 | Kolb et al. |
| 7,004,948 B1 | 2/2006 | Pianca et al. |
| 7,094,234 B1 | 8/2006 | Lennox |
| 7,175,642 B2 | 2/2007 | Briggs et al. |
| 7,204,840 B2 | 4/2007 | Skakoon et al. |
| 7,235,084 B2 | 6/2007 | Skakoon et al. |
| 7,285,287 B2 | 10/2007 | Williams et al. |
| 7,329,262 B2 | 2/2008 | Gill |
| 7,366,561 B2 | 4/2008 | Mills et al. |
| 7,454,251 B2 | 11/2008 | Rezai et al. |
| 7,479,146 B2 | 1/2009 | Malinowski |
| 7,497,863 B2 | 3/2009 | Solar et al. |
| 7,532,661 B2 | 5/2009 | Batra et al. |
| 7,559,935 B2 | 7/2009 | Solar et al. |
| 7,580,756 B2 | 8/2009 | Schulte et al. |
| 7,604,644 B2 | 10/2009 | Schulte et al. |
| 7,636,596 B2 | 12/2009 | Solar |
| 7,637,915 B2 | 12/2009 | Parmer et al. |
| 7,658,879 B2 | 2/2010 | Solar |
| 7,660,621 B2 | 2/2010 | Skakoon et al. |
| 7,699,854 B2 | 4/2010 | Mazzocchi et al. |
| 7,704,260 B2 | 4/2010 | Skakoon et al. |
| 7,744,606 B2 | 6/2010 | Miller et al. |
| 7,803,163 B2 | 9/2010 | Skakoon |
| 7,815,651 B2 | 10/2010 | Skakoon et al. |
| 7,828,809 B2 | 11/2010 | Skakoon et al. |
| 7,833,231 B2 | 11/2010 | Skakoon et al. |
| 7,857,820 B2 | 12/2010 | Skakoon et al. |
| 7,867,242 B2 | 1/2011 | Solar et al. |
| 7,896,889 B2 | 3/2011 | Mazzocchi et al. |
| 7,981,120 B2 | 7/2011 | Mazzocchi et al. |
| 8,116,850 B2 | 2/2012 | Solar |
| 8,192,445 B2 | 6/2012 | Parmer et al. |
| 8,845,656 B2 | 9/2014 | Skakoon et al. |
| 8,911,452 B2 | 12/2014 | Skakoon et al. |
| 2001/0003156 A1 | 6/2001 | Gill |
| 2001/0014771 A1 | 8/2001 | Truwit et al. |
| 2001/0027271 A1 | 10/2001 | Franck et al. |
| 2001/0037524 A1 | 11/2001 | Truwit |
| 2002/0010479 A1 | 1/2002 | Skakoon et al. |
| 2002/0019641 A1 | 2/2002 | Truwit |
| 2002/0022847 A1 | 2/2002 | Ray et al. |
| 2002/0052610 A1* | 5/2002 | Skakoon et al. ............... 606/129 |
| 2002/0077646 A1 | 6/2002 | Truwit et al. |
| 2002/0156372 A1 | 10/2002 | Skakoon et al. |
| 2003/0028199 A1 | 2/2003 | Ghahremani et al. |
| 2003/0079287 A1 | 5/2003 | Truwit |
| 2003/0187351 A1 | 10/2003 | Franck et al. |
| 2003/0199831 A1 | 10/2003 | Morris et al. |
| 2003/0208122 A1 | 11/2003 | Melkent et al. |
| 2004/0026161 A1 | 2/2004 | Takatsuka et al. |
| 2004/0028676 A1 | 2/2004 | Klein et al. |
| 2004/0034367 A1 | 2/2004 | Malinowski |
| 2004/0059260 A1 | 3/2004 | Truwit |
| 2004/0089223 A1 | 5/2004 | Meyer-Fredholm |
| 2004/0105890 A1 | 6/2004 | Klein et al. |
| 2004/0173221 A1 | 9/2004 | Singhal et al. |
| 2004/0176750 A1 | 9/2004 | Nelson et al. |
| 2004/0243146 A1 | 12/2004 | Chesbrough et al. |
| 2004/0243147 A1 | 12/2004 | Lipow |
| 2004/0255991 A1 | 12/2004 | Truwit et al. |
| 2004/0260323 A1 | 12/2004 | Truwit et al. |
| 2004/0267284 A1 | 12/2004 | Parmer et al. |
| 2005/0004602 A1 | 1/2005 | Hart et al. |
| 2005/0054985 A1 | 3/2005 | Mogg |
| 2005/0065535 A1 | 3/2005 | Morris et al. |
| 2005/0125007 A1 | 6/2005 | Gill |
| 2005/0143799 A1 | 6/2005 | Black et al. |
| 2005/0143800 A1 | 6/2005 | Lando et al. |
| 2005/0154297 A1 | 7/2005 | Gill |
| 2005/0182420 A1 | 8/2005 | Schulte et al. |
| 2005/0182421 A1 | 8/2005 | Schulte et al. |
| 2005/0182422 A1 | 8/2005 | Schulte et al. |
| 2005/0182423 A1 | 8/2005 | Schulte et al. |
| 2005/0182424 A1 | 8/2005 | Schulte et al. |
| 2005/0182425 A1 | 8/2005 | Schulte et al. |
| 2005/0182464 A1 | 8/2005 | Schulte et al. |
| 2005/0192594 A1 | 9/2005 | Skakoon et al. |
| 2006/0122627 A1 | 6/2006 | Miller et al. |
| 2006/0192319 A1 | 8/2006 | Solar |
| 2006/0195119 A1 | 8/2006 | Mazzocchi et al. |
| 2007/0250077 A1 | 10/2007 | Skakoon et al. |
| 2007/0250078 A1 | 10/2007 | Stuart |
| 2007/0299427 A1 | 12/2007 | Yeung et al. |
| 2008/0004632 A1 | 1/2008 | Sutherland et al. |
| 2008/0046091 A1 | 2/2008 | Weiss et al. |
| 2008/0058837 A1 | 3/2008 | Steinberg |
| 2008/0082108 A1 | 4/2008 | Skakoon et al. |
| 2010/0145357 A1 | 6/2010 | Lane et al. |
| 2010/0179563 A1 | 7/2010 | Skakoon et al. |
| 2011/0022058 A1 | 1/2011 | Skakoon et al. |
| 2011/0022059 A1 | 1/2011 | Skakoon et al. |
| 2011/0034981 A1 | 2/2011 | Schulte et al. |
| 2013/0197472 A1 | 8/2013 | Skakoon et al. |
| 2015/0100064 A1 | 4/2015 | Skakoon et al. |

FOREIGN PATENT DOCUMENTS

| | | |
|---|---|---|
| DE | 3937052 | 5/1990 |
| DE | 19726141 | 1/1999 |
| DE | 29612100 | 8/1999 |
| DE | 19808220 | 9/1999 |
| DE | 19820808 | 9/1999 |
| DE | 19826078 | 11/1999 |
| EP | 0386936 | 5/1990 |
| EP | 0427358 | 5/1991 |
| EP | 0724865 | 5/1991 |
| EP | 0609085 A1 | 8/1994 |
| EP | 0822844 A1 | 2/1998 |
| EP | 0832611 | 4/1998 |
| EP | 0904741 | 3/1999 |
| EP | 1016432 A2 | 7/2000 |
| EP | 1048318 A2 | 11/2000 |
| EP | 1048320 A2 | 11/2000 |
| EP | 1272120 A2 | 1/2003 |
| EP | 1549241 A2 | 7/2005 |
| EP | 1575440 A1 | 9/2005 |
| EP | 1841378 A2 | 10/2007 |
| EP | 1853191 A2 | 11/2007 |
| EP | 1853192 A2 | 11/2007 |
| GB | 2237993 | 5/1991 |
| GB | 2329473 | 4/1998 |
| GB | 2330080 A | 4/1999 |
| GB | 2342583 A | 4/2000 |
| GB | 2346573 | 8/2000 |
| GB | 2355665 A | 5/2001 |
| GB | 2357700 A | 7/2001 |
| WO | WO-8809151 | 12/1988 |
| WO | WO-9721380 | 12/1988 |
| WO | WO-9522297 | 8/1995 |
| WO | WO-9610368 | 4/1996 |
| WO | WO-9633766 | 10/1996 |
| WO | WO-9703609 | 2/1997 |
| WO | WO-9742870 A1 | 11/1997 |
| WO | WO-9808554 A1 | 3/1998 |
| WO | WO-9817191 | 4/1998 |
| WO | WO-9825535 | 6/1998 |
| WO | WO-9851229 | 11/1998 |

(56) References Cited

FOREIGN PATENT DOCUMENTS

| WO | WO-9955408 A1 | 11/1999 |
|---|---|---|
| WO | WO-0001316 | 1/2000 |
| WO | WO-0018306 | 1/2000 |
| WO | WO-0013743 A1 | 3/2000 |
| WO | WO-0020048 A1 | 4/2000 |
| WO | WO-0124709 | 4/2001 |
| WO | WO-0149197 A1 | 7/2001 |
| WO | WO-0176498 | 7/2001 |
| WO | WO-2001076676 | 3/2002 |
| WO | WO-2001013714 | 8/2002 |
| WO | WO-03068304 A1 | 8/2003 |
| WO | WO-2001076498 A9 | 10/2003 |
| WO | WO-03090820 A1 | 11/2003 |
| WO | WO-2004026161 A2 | 4/2004 |
| WO | WO-2004058086 A1 | 7/2004 |
| WO | WO-2005079903 A2 | 9/2005 |
| WO | WO-2005079912 A1 | 9/2005 |
| WO | WO-2006062892 A2 | 6/2006 |
| WO | WO-2006062806 | 12/2007 |
| WO | WO-2006062824 | 4/2009 |

OTHER PUBLICATIONS

"CRW™—Tyco Healthcare Radionics", Tyco Product Brochure, pp. 1-7.
"Fathom Remote Introducer", Image-Guided Neurologics, Inc., CNS Hynes Convention Center, 2p., (Oct. 30-Nov. 4, 1999).
"Inomed Competence in Neurophysiologic Monitoring", http://www.inomed.com/english/index.htm, (observed Mar. 23, 2004), 2 pgs.
"Leksell Stereotactic System", Elekta Product Brochure, pp. 1-6.
"MicroTargeting® Precision Guidance Using Microelectrode Recording", (Aug. 15, 2003), 5 pgs.
"Possible Existence of Common Internalization Mechanisms among Arginine-rich Peptides", Suzuki, T. et al., Journal of Biological Chemistry, vol. 277, No. 4 (2002) pp. 2437-2443.
"STIMLOC™ by ign," datasheet, NAVIGUS, Image Guided Neurologics, Inc. 2004 (2 pages).
Allison, S., et al., "Microchannel Plate Intensifier Response in Traverse Magnetic Field", Electronic Letters, 26, (Jun. 7, 1990), 770-771.
Drake, J.M., et al. "ISG Viewing Wand System", Neurosurgery, 34 (6), (Jun. 1994), 1094-1097.
Dyer, P.V., et al., "The ISG Viewing Wand: an Application to Atlanto-Axial Cervical Surgery Using the Le for I Maxillary Osteotomy", British Journal of Oral and Maxillofacial Surgery, 33, (1995), 370-374.
European Office Action dated Jan. 22, 2010 for European Application No. 05 852 969.4.
Franck Joel, et al., "microTargeting® Platform System incorporating StarFix™ guidance", microTargeting, pp. 1-44.
Franck, Joel, et al., "microTargeting® Platform incorporating StarFix™ guidance", *microTargeting*, 3 pgs.
Gehring, W. J., "Homeodomain Proteins", Annu. Rev. Biochem., vol. 63 (1997) pp. 487-526.
Gillies, G., et al., "Magnetic Manipulation Instrumentation for Medical Physics Research", Review of Scientific Instruments, 65 (3), Review Article, (Mar. 1994), 533-562.
Grady, M., "Nonlinear Magnetic Stereotaxis:Three-Dimensional, in vivo Remote Magnetic Manipulation of a Small Object in Canine Brain", Medical Physics, 17 (3), (May/Jun. 1990), pp. 405-415.
Grady, M., et al., "Initial Experimental Results of a New Stereotaxic Hyperthermia System", American College of Surgeons: 1998 Clinical Congress: Surgical Forum, 39, (1998), 507-509.
Grady, M., et al., "Magnetic Stereotaxis System for Neurosurgical Procedures", Proc. 37th International Instrumentation Symp., Sand Diego, CA (May 1991), 665-675.
Grady, M., et al., "Magnetic Stereotaxis: A Technique to Deliver Stereotactic Hyperthermia", Neurosurgery, 27 (6), Technical Note, (Dec. 1990), pp. 1010-1016.
Grady, M., et al., "Preliminary Experimental Investigation of in vivo Magnetic Manipulation: Results and Potential Application in Hyperthermia", medical Physics, 16 (2), (Mar./Apr. 1989), pp. 263-272.
Hata, N., et al., "Needle Insertion Manipulator for CT-and MR-Guided Stereotactic Neurosurgery", Interventional MR:Techniques and Clinical Experience, St. Louis: London: Mosby; Martin Dunitz, F. Jolesz and I. Young, eds., (1998), 99-106.
Hirschberg, H., et al., "Image-Guided Neurosurgery—MR compatible stereotactic equipment", http:www.medinnova.no/English/P51466ster.html. (Mar. 29, 2001), 1p.
Hirschberg, Henry, et al., "Image-guided neurosurgery", *stereotactic equipment for MR imaging*, http://www.medinnova.no/English/P51466ster.html, (Observed Mar. 8, 2002), 1 page.
Howard, M., et al., "Magnetic Movement of a Brain Thermocepter", Neurosurgery, 24 (3), (1989), 444-448.
Howard, M., et al., "Magnetic Neurosurgery", Stereotactic and Functional Neurosurgery, 66, (1996), 102-107.
Howard, M., et al., "Magnetic Neurosurgery: Image-Guided, Remote-Controlled Movement of Neurosurgical Implants", Ch. 26 in: Clinical Neurosurgery: Proceedings of the Congress of Neurological Surgeons, San Francisco, CA, (1995), 382-391.
Howard, M., et al., "Review of Magnetic Neurosurgery Research", J. Image Guided Surgery, 1, (Nov. 1995), 295-299.
International Search Report and Written Opinion for PCT/US05/43651 dated May 8, 2008.
Lawson, M., et al., "Near Real-Time Bi-planar Fluoroscopic Tracking System for the Video Tumor Fighter", SPIE, 1445, (1991), 265-275.
Leggett, W.B., et al. "Surgical Technology—The Viewing Wand: A New System for Three-Dimensional Computed Tomography-Correlated Intraoperative Localization", Current Surgery, (Dec. 1991), 674-678.
Malison, R.T., et al., "Computer-Assisted Coregistration of Multislice SPECT and MR Brain Images by Fixed External Fiducials", Journal of Computer Assisted Tomography, 17 (6), (1993), pp. 952-960.
Mannervik, M., "Target genes of homeodomain proteins", BioEssays vol. 21.4 (Apr. 1999) pp. 267-270.
McNeil., R., et al., "Characteristics of an Improved Magnetic-Implant Guidance System", IEEE Transactions on Biomedical Engineering, 42 (8), (Aug. 1995), 802-808.
McNeil., R., et al., "Functional Design Features and Initial Performance Characteristics of a Magnetic-Implant Guidance System for Stereotactic Neurosurgery", IEEE Transactions on Biomedical Engineering, 42 (8), (1995), 793-801.
Meeker, D., et al., "Optimal Realization of Arbitrary Forces in a Magnetic Stereotaxis System," IEEE Transactions on Magnetics, 32 (2), (Mar. 1996), 320-328.
Molloy, J., et al., "Experimental Determination of the Force Required for Insertion of a Thermoseed into Deep Brain Tissues", Annals of Biomedical Engineering, 18, (1990), 299-313.
Molly, J., et al., "Thermodynamics of Movable Inductively Heated Seeds for the Treatment of Brain Tumors", Medical Physics, 18 (4), (1991), 794-803.
Office Action dated Jul. 19, 2012 for U.S. Appl. No. 12/899,677, filed Oct. 7, 2010.
Office Action dated Jul. 2, 2013 for U.S. Appl. No. 12/899,674, filed Oct. 7, 2010.
Office Action dated Nov. 6, 2013 for U.S. Appl. No. 12/730,724, filed Mar. 24, 2010.
Oliver, L., "Cup-and-Ball Chemopallidectomy Apparatus", (1958), p. 401.
Patikoglou, G. et al., "Eukaryotic Transcription Factor-DNA Complexes", Annual Review of Biophysics and Biomolecular Structure vol. 26 (1997) pp. 289-325.
Quate, E., et al., "Goniometric Motion Controller for the Superconducting Coil in a Magnetic Stereotaxis System", IEEE Transactions on Biomedical Engineering, 38 (9), (Sep. 1991), 899-905.

(56) References Cited

OTHER PUBLICATIONS

Ramos, P., et al., "Electro-Optic Imaging Chain for a Biplanar Fluoroscope for Neurosurgery: Magnetic Field Sensitivity and Contrast Measurements", Optical Engineering 32, (7), (1993), 1644-1656.
Ramos, P., et al., "Low-Dose, Magnetic Field-Immune, Bi-Planar Fluoroscopy for Neurosurgery", Proc. SPIE, 1443 (Medical Imaging V: Image Physics), (1991), 160-170.
Ramos, P., et al., "Microchannel Plate Image Intensifier Electron Dynamics in Magnetic Field", Electronics Letters, 27 (18), (Aug. 29, 1991), pp. 1636-1638.
Ritter, R., et al., "Magnetic Stereotaxis: Computer-Assisted, Image-Guided Remote Movement of Implants in the Brain", Ch. 26 in: Computer-Integrated Technology and Clinical Applications, MIT Press, Cambridge, MA., Taylor, R., et al., eds., (1996), 363-369.
Ritter, R., et al., "Magnetic Sterotaxis: An Application of Magnetic Control Technology to the Needs of Clinical Medicine", Proc. of the MAG'95 Industrial Conf. and Exhibition, Technomic Pub. Co., Lancaster, PA., Allaire, P., ed., (1995), 186-193.
Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.
Sandeman, D.S., et al., "Advances in image-directed neurosurgery: Preliminary experience with the ISG Viewing Wand compared with the Leksell G frame", British Journal of Neurosurgery, 8 (199), pp. 529-544.
Stein, S. et al., "Checklist: Vertebrate homeobox genes", Mechanisms of Development, vol. 55, No. 1 (Mar. 1996) pp. 91-108.
Supplementary European Search Report dated Oct. 26, 2009 for EP05852969 filed Dec. 6, 2005 claiming benefit of U.S. Appl. No. 11/005,907, filed Dec. 5, 2004.
Szikora, I., et al., "Endovascular Treatment of Experimental Aneurysms with Liquid Polymers: The Protective Potential of Stents", Neurosurgery, 38, (Feb. 1996), 339-347.
Vollmer, J. et al., "Homeobox Genes in the Developing Mouse Brain", Journal of Neurochemistry, vol. 71, No. 1 (Jul. 1998) pp. 1-19.
Wolberger, C., "Homeodomain Interactions", Current Opinion in Structural Biology vol. 6, No. 1 (Feb. 1996) pp. 62-68.
Yeh, H.S., et al., "Implantation of intracerebral depth electrodes for monitoring seizures using the Pelorus stereotactic system guided by magnetic resonance imaging", J. Neurosurg., 78 (1993), pp. 138-141.
Zinreich, S.J., et al., "Frameless Sterotaxic Integration of CT Imaging Data: Accuracy and Initial Applications", Radiology, 188 (3), (1993), pp. 735-742.
"The ISG Viewing Wand: an application to atlanto-axial cervical surgery using the Le Fort I maxilary osteotomy", British Journal of Oral and Maxillofacial Surgery, 33, (1995) pp. 370-374.
Beld, Marcel, et al. "Quantitative Antibody Responses to Structural (Core) and Nonstructural (NS3, NS4, and NS5) Hepatitis C Virus Proteins Among Seroconverting Injecting Drug Users: Impact of Epitope Variation and Relationship to Detection of HCV RNA in Blood." (1999) Hepatology vol. 29, No. 4. pp. 1288-1298.
Franck, Joel, et al., "microTargeting® Platform System incorporating StarFix™ guidance", microTargeting, pp. 1-44.
Guardian™ Cranial Burr Hole Cover System—Clinician's Manual. ANS A St. Jude Medical Companybrochure. Apr. 2009. pp. 1 -15.
International Preliminary Examination Report for PCT/US01/11178 completed Jul. 18, 2002, claiming benefit of U.S. Appl. No. 60/195,663, filed Apr. 7, 2000.
International Preliminary Examination Report dated Nov. 25, 2002 for PCT/US01/25904 filed Aug. 17, 2001 claiming benefit of U.S. Appl. No. 60/225,952, filed Aug. 17, 2000.
International Preliminary Report on Patentability and Written Opinion issued Aug. 14, 2006 for PCT/US2005/003970 which claims benefit of U.S. Appl. Nos. 60/544,456; 60/563,787; 60/587,356; 60/602,749; as does U.S. Appl. No. 12/899,679, filed Oct. 7, 2010.
International Preliminary Report on Patentability and Written Opinion dated Feb. 10, 2009 for PCT/US2005/004141 which claims benefit of U.S. Appl. Nos. 60/544,456; 60/563,787; 60/587,356; 60/602,749; as does U.S. Appl. No. 11/054,199, filed Feb. 9, 2005 and U.S. Appl. No. 12/899,679, filed Oct. 7, 2010.
International Preliminary Report on Patentability for PCT/US2005/043913 dated Mar. 17, 2009, claiming benefit of U.S. Appl. No. 11/005,907, filed Dec. 6, 2004.
International Search Report and Written Opinion dated Jun. 21, 2005 for PCT/US2005/004141 which claims benefit of U.S. Appl. Nos. 60/544,456; 60/563,787; 60/587,356; 60/602,749; as does U.S. Appl. No. 11/054,199, filed Feb. 9, 2005 and U.S. Appl. No. 12/899,679, filed Oct. 7, 2010.
International Search Report and Written Opinion dated Jun. 3, 2005 for PCT/US2005/003970 which claims benefit of U.S. Appl. Nos. 60/544,456; 60/563,787; 60/587,356; 60/602,749; as does U.S. Appl. No. 11/054,199, filed Feb. 9, 2005 and U.S. Appl. No. 12/899,679, filed Oct. 7, 2010.
International Search Report and Written Opinion dated May 8, 2008 for PCT/US05/43651 claiming benefit of U.S. Appl. No. 11/262,298, filed Oct. 28, 2005 and U.S. Appl. No. 11/005,607, filed Dec. 4, 2004.
International Search Report and Written Opinion dated Nov. 5, 2007 for PCT/US05/43532 claiming benefit of U.S. Appl. No. 11/005,605, filed Dec. 4, 2004.
International Search Report for PCT/US01/11178 dated Feb. 13, 2002, claiming benefit of U.S. Appl. No. 60/195,663, filed Apr. 7, 2004.
International Search Report for PCT/US05/43913 dated Oct. 3, 2008, claiming benefit of U.S. Appl. No. 11/005,907, filed Dec. 6, 2004.
International Search Report dated Dec. 19, 2001 for PCT/US01/25904 claiming benefit of U.S. Appl. No. 60/225,952, filed Aug. 17, 2000.
International Search Report dated May 28, 2004 for PCT/US03/40610 claiming benefit of U.S. Appl. No. 10/325,615, filed Dec. 20, 2002.
International Search Report dated May 3, 2004 for PCT/US03/28966 claiming benefit of U.S. Appl. No. 60/411,309, filed Sep. 17, 2002.
International Search Report dated Oct. 24, 2001 for PCT/US01/40458 claiming benefit of U.S. Appl. No. 60/195,663, filed Apr. 7, 2000.
Invitation to Pay Additional Fees dated Jan. 15, 2004 for PCT/US03/028966 filed Sep. 17, 2003 claiming benefit of U.S. Appl. No. 60/411,309, filed Sep. 17, 2002.
Malison, R. T., et al., "Computer-Assisted Coregistration of Multislice SPECT and MR Brain Images by Fixed External Fiducials", Journal of Computer Assisted Tomography, 17 (6) (1993) pp. 952-960.
McHugh, Thomas M., et al. "The Sensitive Detection and Quantitation of Antibody to HCV by Using a Microsphere-Based Immunoassay and Flow Cytometry." (1997) Cytometry 29:106-112.
Notice of Allowance dated Jul. 9, 2010 for U.S. Appl. No. 11/768,077, filed Jun. 25, 2007.
Notice of Allowance dated Jul. 6, 2010 for U.S. Appl. No. 11/768,554, filed Jun. 26, 2007.
Office Action dated Apr. 12, 2011 for U.S. Appl. No. 11/054,649, filed Feb. 9, 2005.
Office Action dated Apr. 14, 2010 for U.S. Appl. No. 11/054,649, filed Feb. 9, 2005.
Office Action dated Apr. 29, 2008 for U.S. Appl. No. 11/054,649, filed Feb. 9, 2005.
Office Action dated Apr. 7, 2008 for U.S. Appl. No. 11/054,583, filed Feb. 9, 2005.
Office Action dated Aug. 25, 2009 for U.S. Appl. No. 11/054,649, filed Feb. 9, 2005.
Office Action dated Aug. 30, 2010 for U.S. Appl. No. 11/054,199, filed Feb. 9, 2005.
Office Action dated Dec. 23, 2009 for U.S. Appl. No. 11/768,077, filed Jun. 25, 2007.
Office Action dated Dec. 9, 2008 for U.S. Appl. No. 11/054,649, filed Feb. 9, 2005.

(56) References Cited

OTHER PUBLICATIONS

Office Action dated Feb. 18, 2010 for U.S. Appl. No. 11/054,199, filed Feb. 9, 2005.
Office Action dated Jul. 23, 2008 for U.S. Appl. No. 11/054,073, filed Feb. 9, 2005.
Office Action dated Nov. 10, 2010 for U.S. Appl. No. 11/054,649, filed Feb. 9, 2005.
Office Action dated Nov. 23, 2009 for U.S. Appl. No. 11/768,554, filed Jun. 26, 2007.
Office Action dated Feb. 9, 2016 for U.S. Appl. No. 12/730,724, filed Mar. 24, 2010.
Office Action dated Aug. 22, 2016 for U.S. Appl. No. 12/730,724, filed Mar. 24, 2010.
Office Action dated Jul. 29, 2016 for U.S. Appl. No. 12/899,679, filed Oct. 7, 2010.
Office Action dated Feb. 9, 2017 for U.S. Appl. No. 12/899,679, filed Oct. 7, 2010.

* cited by examiner

LOW PROFILE INSTRUMENT IMMOBILIZER

CROSS REFERENCE TO RELATED APPLICATIONS

This application is a divisional of U.S. application Ser. No. 12/730,724 filed Mar. 24, 2010, now U.S. Pat. No. 9,901,713, which is a divisional of U.S. application Ser. No. 11/005,907 filed Dec. 6, 2004, now U.S. Pat. No. 7,704,260, which claims benefit of PCT/US2003/028966 filed Sep. 17, 2003, which claims benefit of U.S. Provisional Application No. 60/411,309 filed Sep. 17, 2002. The entire disclosures of each of the above applications are incorporated herein by reference.

FIELD OF THE INVENTION

This document relates generally to instrument immobilizers, and more specifically, but not by way of limitation, to a low profile instrument immobilizer.

BACKGROUND

Neurosurgery sometimes involves inserting an electrode (for recording brain signals or providing stimulating pulses) or other instrument (for example, a catheter for fluid aspiration or drug infusion) through a burr hole or other entry portal into a subject's brain toward a target region of the brain. In certain applications, there is a need to secure the electrode or other instrument in place after it has been introduced, potentially for an extended period of time. Moreover, in certain applications, other equipment (such as a trajectory guide and any associated equipment) is mounted to the patient's skull about the burr hole.

For these and other reasons, which will become apparent upon reading the following detailed description and viewing the drawings that form a part thereof, the present inventors have recognized an unmet need for low profile instrument immobilizer devices, tools, and methods that reduce or avoid patient discomfort and also better retain instruments.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

FIGS. 1-5 and 22 illustrate various views of a first embodiment of a low-profile instrument immobilizer for securing a flexible recording or stimulating electrode or the like, or other instrument (such as a catheter for fluid aspiration or drug, cell, or substance infusion) after it has been introduced through a burr hole or other entry portal to a desired target location in the brain.

Figure 1:
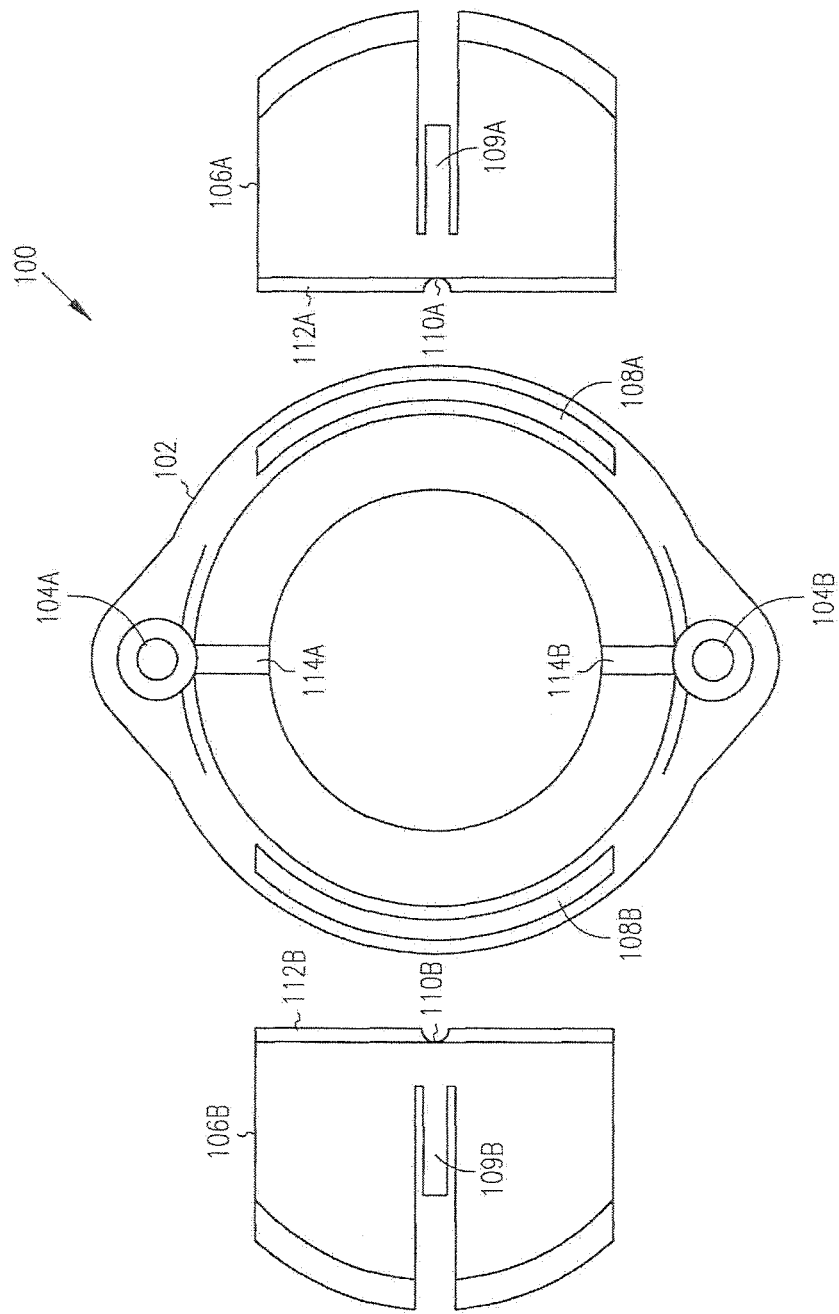
FIG. 1 is a top view illustrating generally, by way of example, but not by way of limitation, portions of a first instrument immobilizer.

FIG. 1 is a top view illustrating generally, by way of example, but not by way of limitation, portions of instrument immobilizer 100. In this example, instrument immobilizer 100 includes a hoop-like base 102 (also referred to herein as a "hoop"). The hoop 102 is sized and shaped for being circumferentially disposed about a burr hole (which, in this document, is understood to include a twist drill hole) or other entry portal of a desired size. Burr holes typically range in diameter between about 6 millimeters to about 14 millimeters. In this example, hoop 102 includes holes 104A-B or other passages for receiving corresponding bone screws or the like therethrough for securing hoop 102 to a subject's skull (or other desired location upon the subject). In this example, hole 104A is located on an opposite side of hoop 102 from hole 104B. In operation, hoop 102 is secured to the skull before the electrode or other instrument is inserted to the desired location in the patient's brain. The electrode or other instrument (for example an aspiration catheter or an infusion catheter) is inserted through the circular center passage defined by hoop 102.

In this example, instrument immobilizer 100 includes a two-piece sliding cover including cover pieces 106A-B. Each cover piece 106A-B is sized and shaped to be inserted through a corresponding side slot 108A-B in an opposing side of hoop 102. Each piece of cover piece 106A-B also has a snap-fit or other catch 109A-B, such as a deformable tab, that engages a portion of hoop 102 when that cover piece 106A or 106B has been fully inserted. Catches 109A-B hold their corresponding cover piece 106A-B in place after it has been fully inserted. Alternatively, the instrument immobilizer includes a one-piece sliding cover that, in one example, the single cover piece substantially covers the circular center passage when fully inserted through a corresponding side slot.

Figure 2:
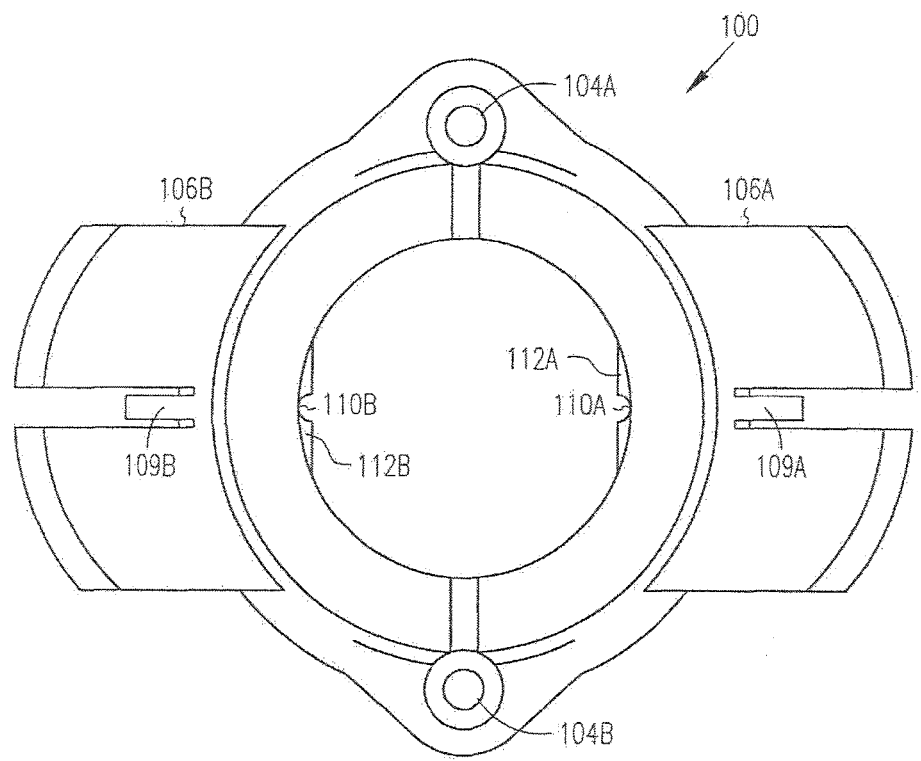
FIG. 2 is a top view illustrating generally an example of portions of the first instrument immobilizer after cover pieces have been partially inserted into respective slots in opposing sides of a hoop.
Figure 3:
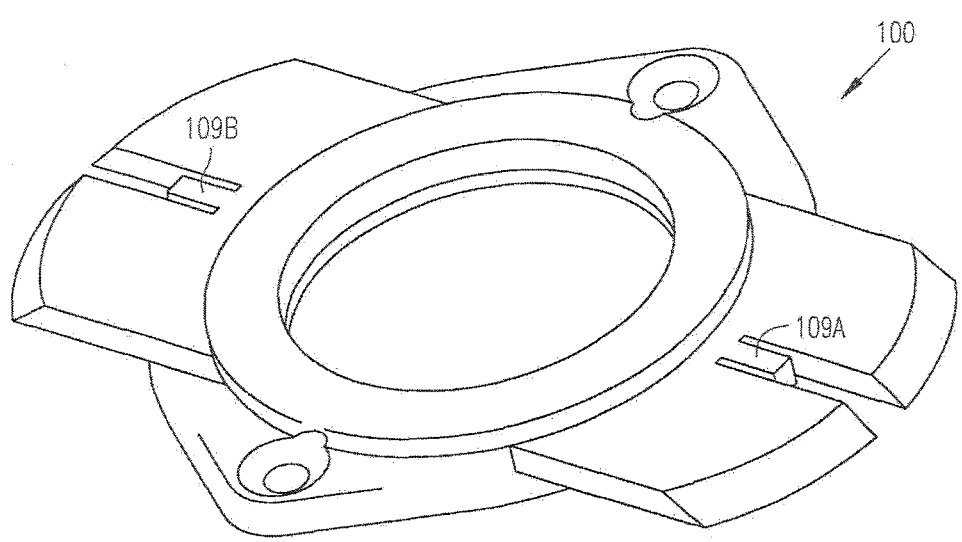
FIG. 3 is a perspective view illustrating generally an example of portions of the first instrument immobilizer after the cover pieces have been partially inserted into the respective slots of the hoop.
Figure 4:
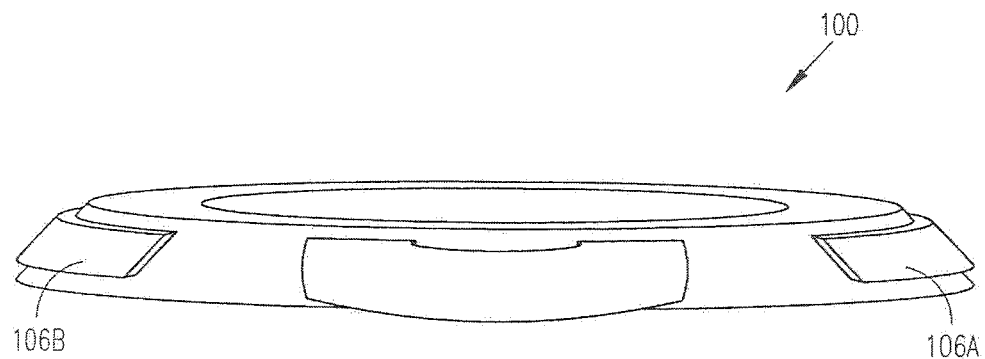
FIG. 4 is a side view illustrating generally an example of portions of the first instrument immobilizer after the cover pieces have been almost fully inserted into the respective slots of the hoop.
Figure 5:
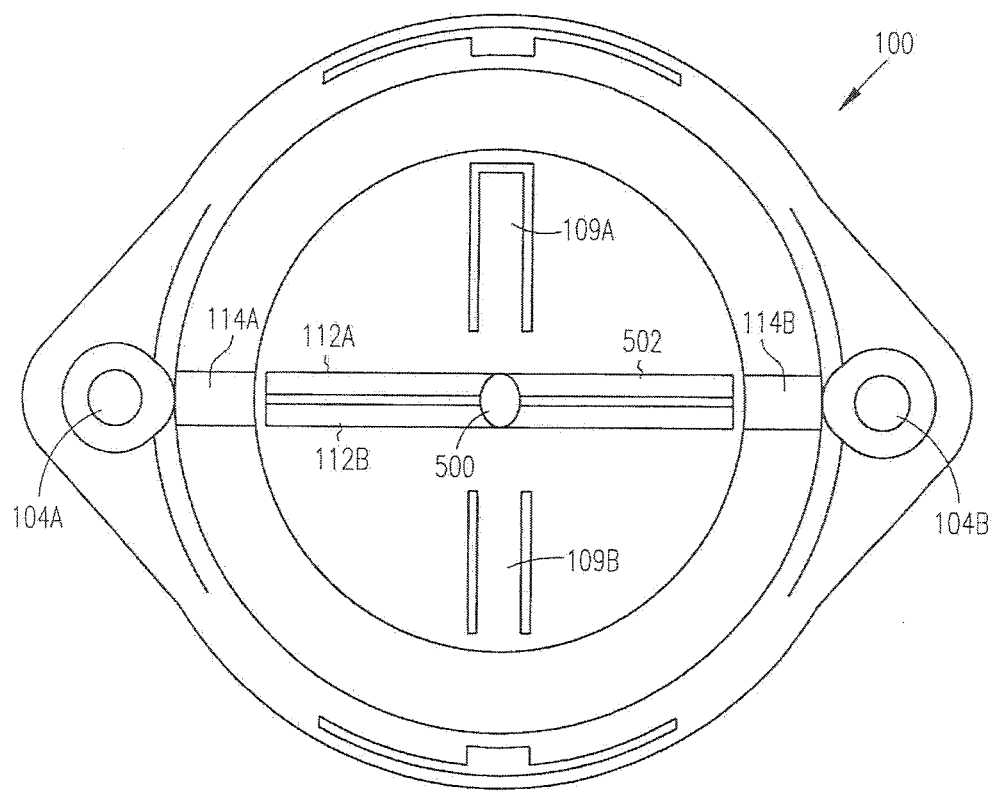
FIG. 5 is a top view illustrating generally an example of portions of the first instrument immobilizer after the cover pieces have been fully inserted into the respective slots of the hoop.

FIG. 2 is a top view illustrating generally an example of portions of instrument immobilizer 100 after cover pieces 106A-B have been partially inserted into respective slots 108A-B in opposing sides of hoop 102. FIG. 3 is a perspective view illustrating generally an example of portions of instrument immobilizer 100 after cover pieces 106A-B have been partially inserted into respective slots 108A-B of hoop 102. FIG. 4 is a side view illustrating generally an example of portions of instrument immobilizer 100 after cover pieces 106A-B have been almost fully inserted into respective slots 108A-B of hoop 102. FIG. 5 is a top view illustrating generally an example of portions of instrument immobilizer 100 after cover pieces 106A-B have been fully inserted into respective slots 108A-B of hoop 102.

As illustrated generally in FIGS. 1-5, when cover pieces 106A-B have been fully inserted and pressed against each other, they substantially cover the center passage defined by hoop 102, except for a small circular opening 500 formed by aligned semi-circular cutouts 110A-B of cover pieces 106A-B. Also, when cover pieces 106A-B have been fully inserted and their respective beveled edges 112A-B are pressed against each other, a resulting trough, channel or groove 502 is formed. In this example, groove 502 aligns with exit grooves 114A-B in hoop 102, however, this is not required. In another example, one or more exit grooves 114A-B are disposed elsewhere about hoop 102, such as, for example, exit grooves 114 distributed about hoop 102 at regular intervals (e.g., every 30 degrees, etc.). Moreover, such differently disposed exit grooves 114 are also applicable to all of the other examples depicted and/or described in this document.

Figure 22:
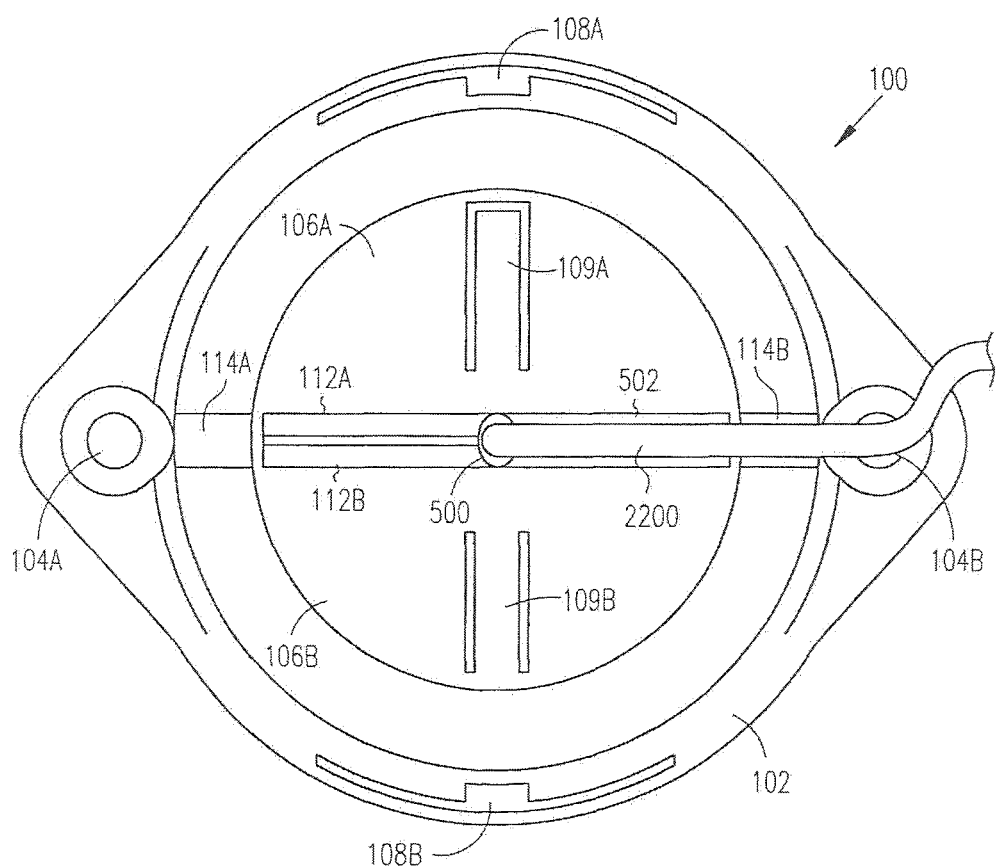
FIG. 22 is a top view illustrating generally the first instrument immobilizer where the cover pieces immobilize an instrument.

FIG. 22 is a top view illustrating an instrument immobilizer 100 retaining at least one wire electrode or other introduced instrument 2200 (e.g., a catheter). Once the instrument 2200 is retained by cover pieces 106A-B so as to immobilize the instrument, a portion of the instrument 2200 may be bent into a portion of groove 502 and one of exit grooves 114A-B to laterally exit hoop 102. In the above described example having multiple exit grooves 114A-B, the instrument 2200 may be bent into any one of the exit grooves 114A-B. The introduced instrument 2200 is retained and immobilized by the snug fit through opening 500. Additionally the instrument 2200 is further retained by snug positioning of a portion of the instrument 2200 within the groove 502 and one of the exit grooves 114A-B. Where the instrument 2200 is positioned within an exit groove 114A-B the instrument immobilizer 100 and instrument 2200, in one example, are covered by a cap that provides a semi-permanent fixture for both.

FIGS. 6-9 and 23 illustrate various views of a second embodiment of a low-profile instrument immobilizer for securing a flexible recording or stimulating electrode or the like (or other instrument, such as a catheter) after it has been introduced through a burr hole or other entry portal to a desired target location in the brain.

Figure 6:
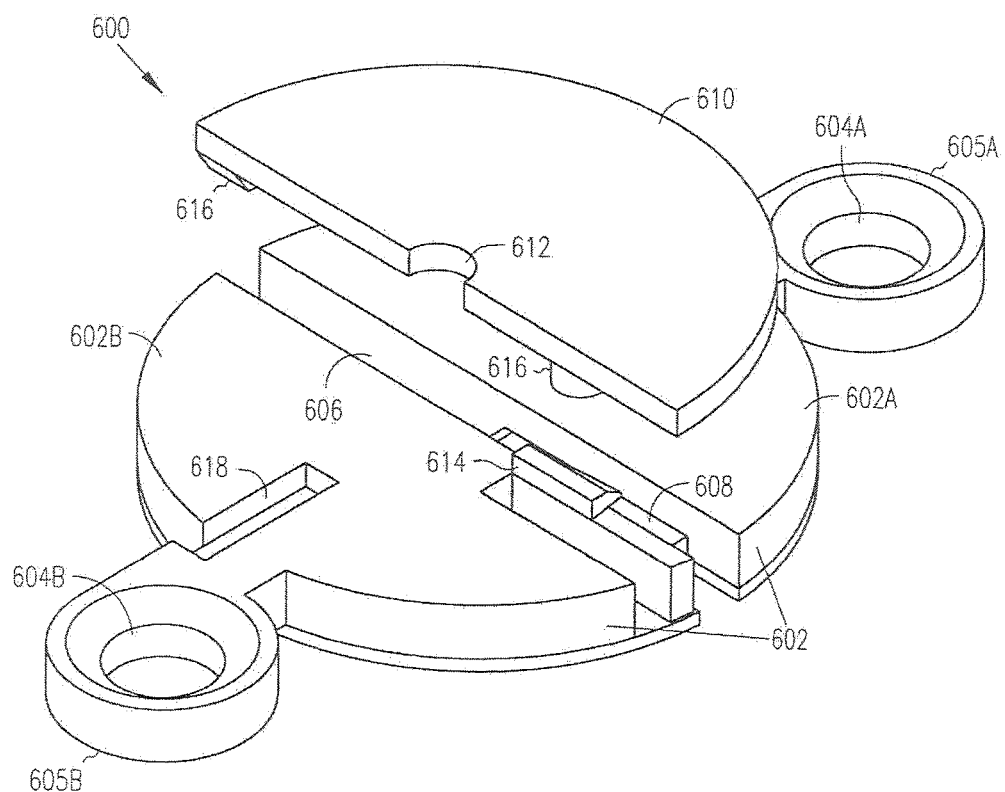
FIG. 6 is a perspective view illustrating generally, by way of example, but not by way of limitation, portions of a second instrument immobilizer.

FIG. 6 is a perspective view illustrating generally, by way of example, but not by way of limitation, portions of instrument immobilizer 600. In this example, instrument immobilizer 600 includes a base 602 sized and shaped for being secured above and covering a similarly-sized burr hole or other entry portal. In this example base 602 includes a pair of semicircular pieces 602A-B. Base 602 includes holes 604A-B or other passages for receiving corresponding bone screws or the like therethrough for securing base 602 to a subject's skull (or other desired location upon the subject). In this example, hole 604A is located on an opposite side of base 602 from hole 604B. The holes 604A-B are, in this example, located on members 605A-B, which extend radially outward from base 602. In one example of operation, base 602 is secured to the skull by inserting a screw through one of the holes 604A-B. This permits the instrument immobilizer 600 to rotate about the axis of the screw through the one of the holes 604A-B. The instrument immobilizer 600 is rotated away from the burr hole in this manner, thereby providing access to the burr hole. The electrode or other instrument is inserted through the burr hole to the target location, as desired. The instrument immobilizer is then rotated back toward the burr hole about the axis of the screw through the one of the holes 604A-B such that the instrument extends through an access slot 606. The instrument can then be further secured, such as discussed below.

In this example, the access slot 606 extends across base 602, except for the presence of connecting member 608. The slot 606 permits access to the underlying burr hole or other entry portal, except for the obstruction of connecting member 608. Connecting member 608 provides a mechanical connection between two semicircular portions 602A-B of base 602. The semicircular portions 610A-B are separated by slot 606 and connecting member 608.

In this example, a latch 610 is eccentrically coupled to base 602 by coupling the latch to the base at a point offset from the center of the base. In the example of FIG. 6, the latch includes a semicircular latch piece 610 having a post 616 that is snap-fit into semicircular piece 602A of base 602. FIG. 6 illustrates latch piece 610 in an eccentrically-mounted open position. In this example, latch piece 610 includes a semicircular notch or cutout 612 that is sized to retain the electrode or other instrument snugly within slot 606 when latch piece 610 is moved to the closed position.

Figure 7:
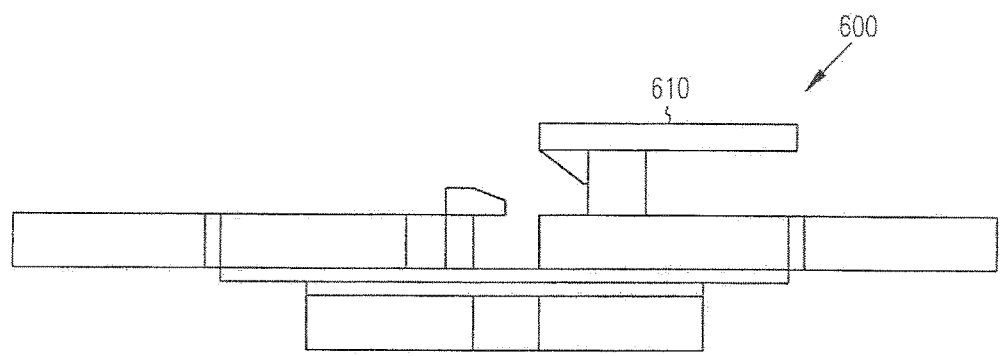
FIG. 7 is a side view of the second instrument immobilizer with a latch piece in an open position.
Figure 8:
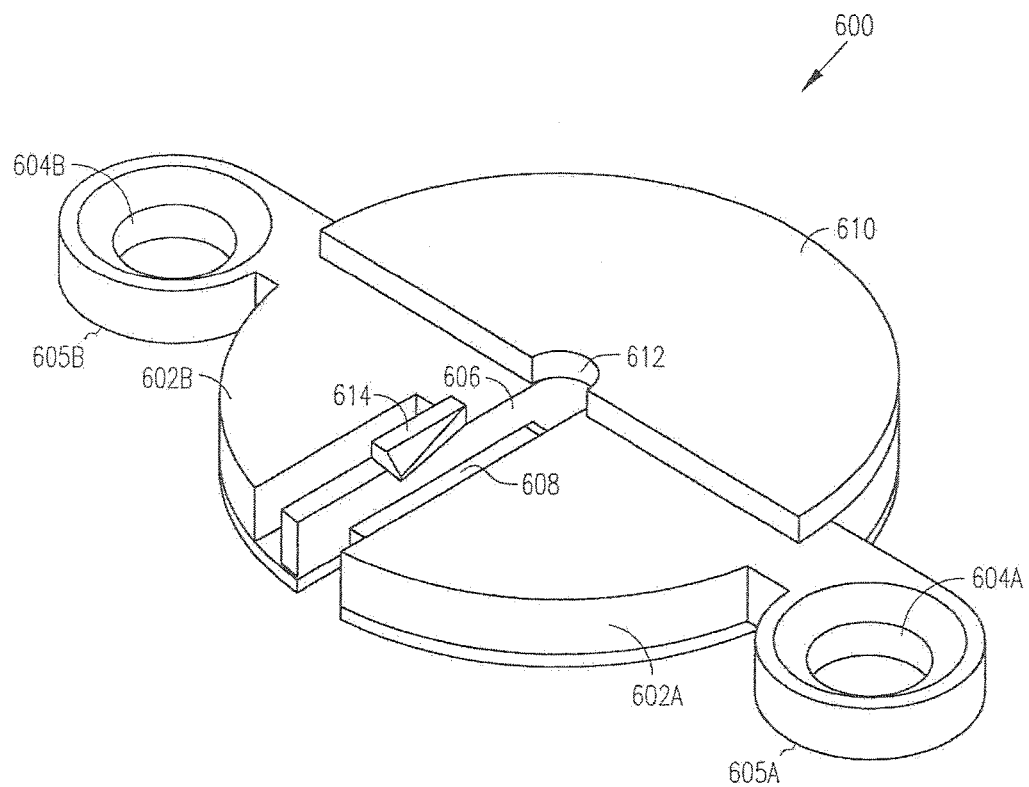
FIG. 8 is a perspective view of the second instrument immobilizer with the latch piece in a closed position.
Figure 9:
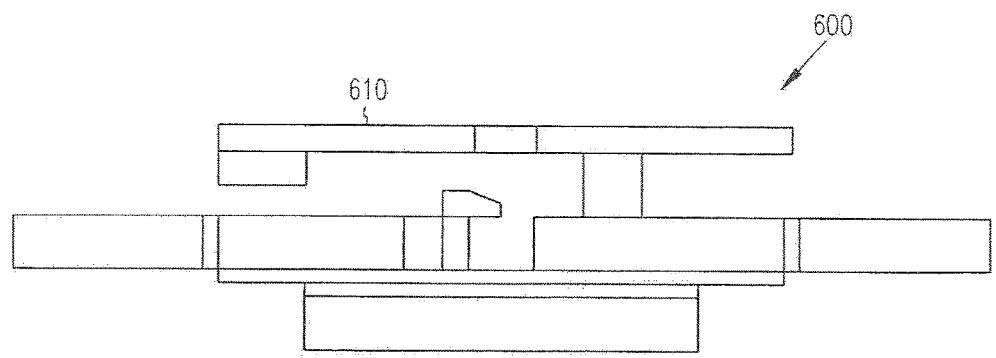
FIG. 9 is a side view of the second instrument immobilizer with the latch piece in a closed position.

After the instrument is axially positioned as desired within the slot 606, then the latch piece 610 is moved to the closed position and immobilizes the instrument. FIG. 7 is a side view of instrument immobilizer 600 with latch piece 610 in the open position. FIG. 8 is a perspective view of instrument immobilizer 600 with latch piece 610 in the closed position. FIG. 9 is a side view of instrument immobilizer 600 with latch piece 610 in the closed position.

In FIGS. 6-9, when latch piece 610 is in the closed position the semicircular shape of latch piece 610 aligns and conforms with the circumference of base 602 such that the peripheral profile of the latch piece 610 is coextensive with the peripheral profile of the base 602 when the immobilizer 600 is viewed from above.

Figure 23:
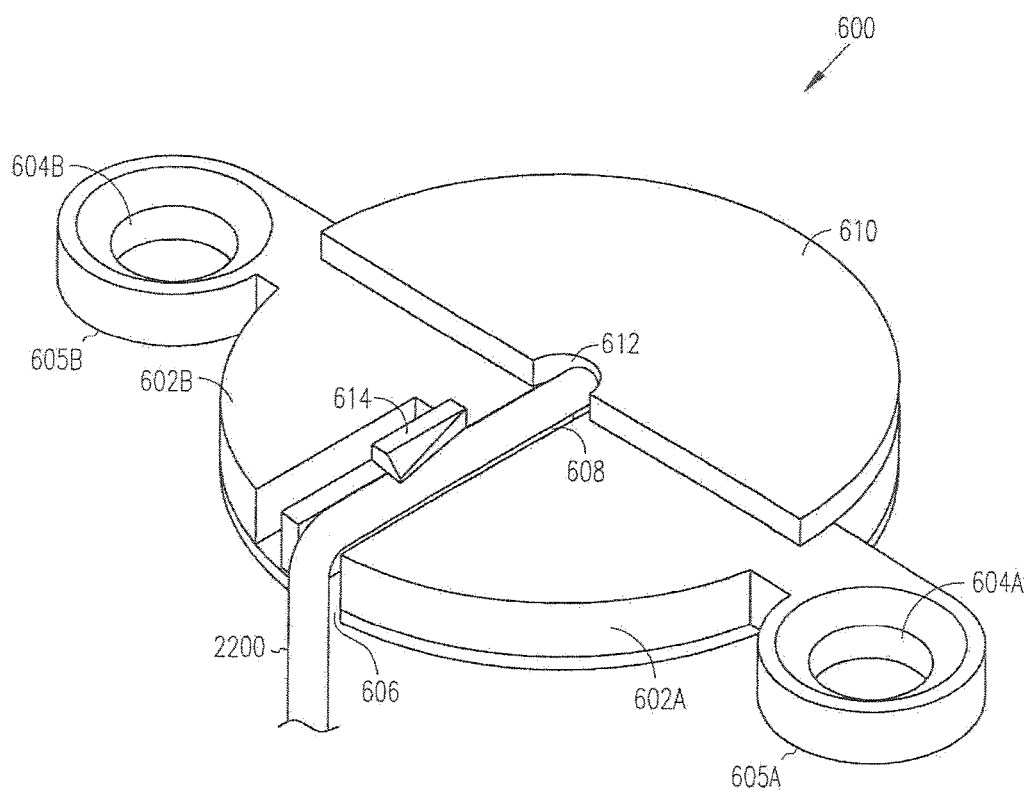
FIG. 23 is a perspective view of the second instrument immobilizer with the latch piece in the closed position where the latch piece immobilizes an instrument.

FIG. 23 is a perspective view illustrating the instrument immobilizer retaining a wire electrode or other introduced instrument 2200 (for example a catheter as described above). In the closed position, the instrument 2200 is snugly retained within the semicircular cutout 612 between latch piece 610 and connecting member 608. In this example, the latch piece 610 is securable in the closed position by a detent 616 that extends from a lower surface of the latch piece 610. As generally shown in FIG. 6, the detent 616 engages the base 602 within a securing slot 618 defined by the base to secure the latch piece 610 in the closed position. The instrument 2200 may be laterally bent (e.g., such as at about a 90 degree angle, or otherwise) to laterally exit base 602. In this example, the laterally bent portion of the instrument 2200 may be wedged snugly under or along a tab (such as retaining member 614) disposed above slot 606. This further secures the instrument 2200 after immobilization by the latch piece 610.

FIGS. 10-14 illustrate various views of a third embodiment of a low-profile instrument immobilizer for securing a flexible recording or stimulating electrode or the like, or other instrument, after it has been introduced through a burr hole or other entry portal to a desired target location in the brain.

Figure 10:
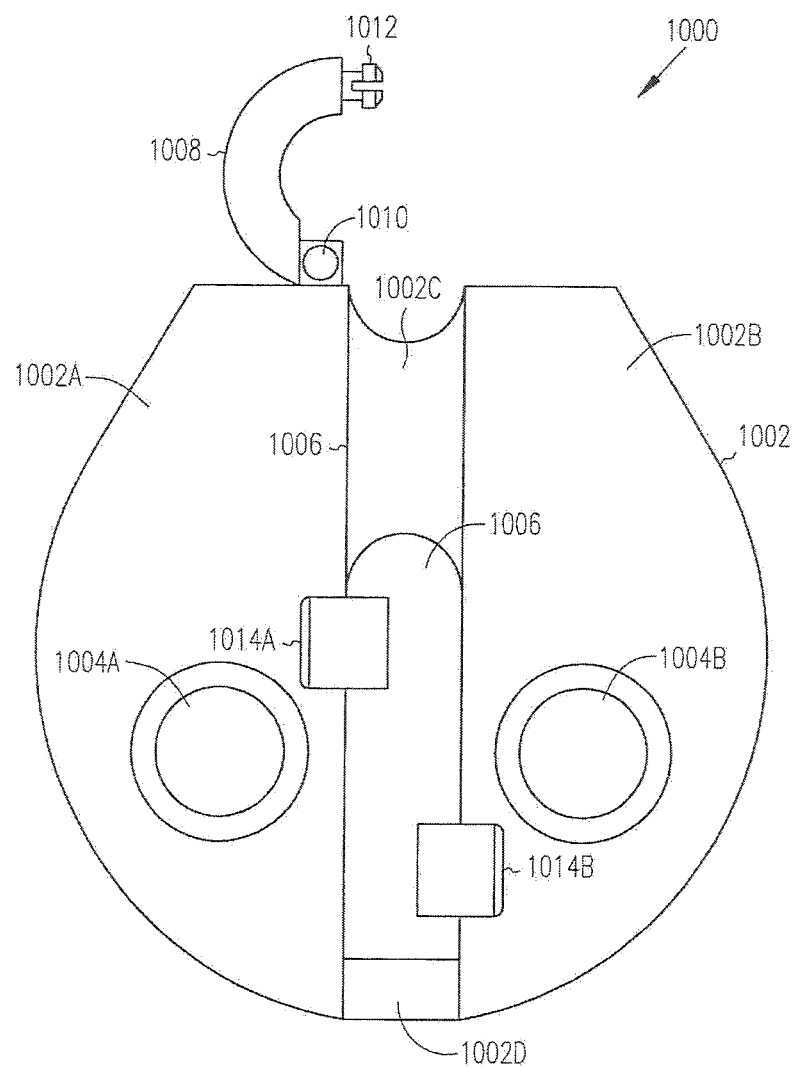
FIG. 10 is a top view of a third instrument immobilizer.

FIG. 10 is a top view illustrating generally, by way of example, but not by way of limitation, portions of instrument immobilizer 1000. In this example, instrument immobilizer 1000 includes a base 1002 sized and shaped for being secured such that it is cantilevered over at least a portion of a burr hole or other entry portal. In this example base 1002 includes a pair of approximately semicircular portions 1002A-B connected by connecting member portions 1002C-D. Base 1002 includes holes 1004A-B or other passages for receiving corresponding bone screws or the like therethrough for securing base 1002 to a subject's skull (or other desired location upon the subject). An optional slot or lateral groove 1006 extends between semicircular portions 1002A-B and connecting member portions 1002C-D of base 1002.

In this example, instrument immobilizer 1000 includes a semicircular shaped clasp 1008. The clasp 1008 is coupled at a first end to one of the semicircular portions 1002A-B by a hinge 1010. At a second end, the clasp 1008 includes a fastener 1012. In this example, the fastener 1012 includes a male snap-fitting, for securing to a mating female receptacle 1100 (FIG. 11) in the other of the semicircular portions 1002A-B when the clasp 1008 is moved from an open position to a closed position. In another example, the clasp 1008 is coupled at a first end to one of the semicircular portions 1002A-B with a flexible element, including but not limited to deformable plastic, or a hinge as described above.

Figure 11:
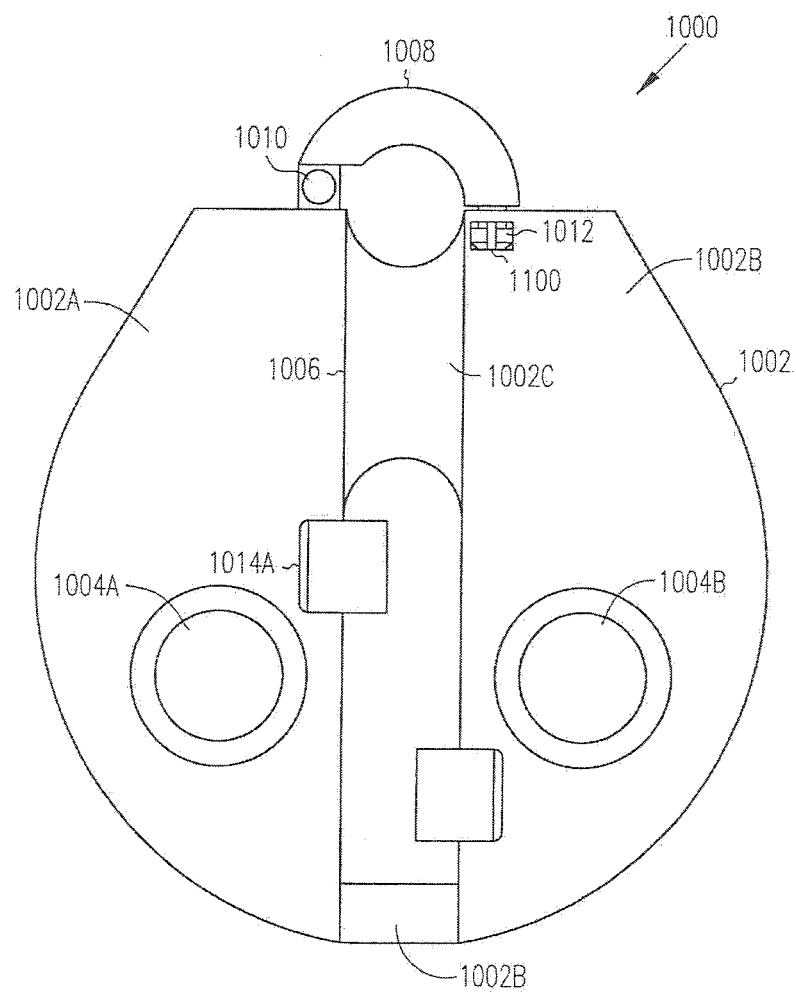
FIG. 11 is a top view of the third instrument immobilizer with a clasp in a closed position.
Figure 12:
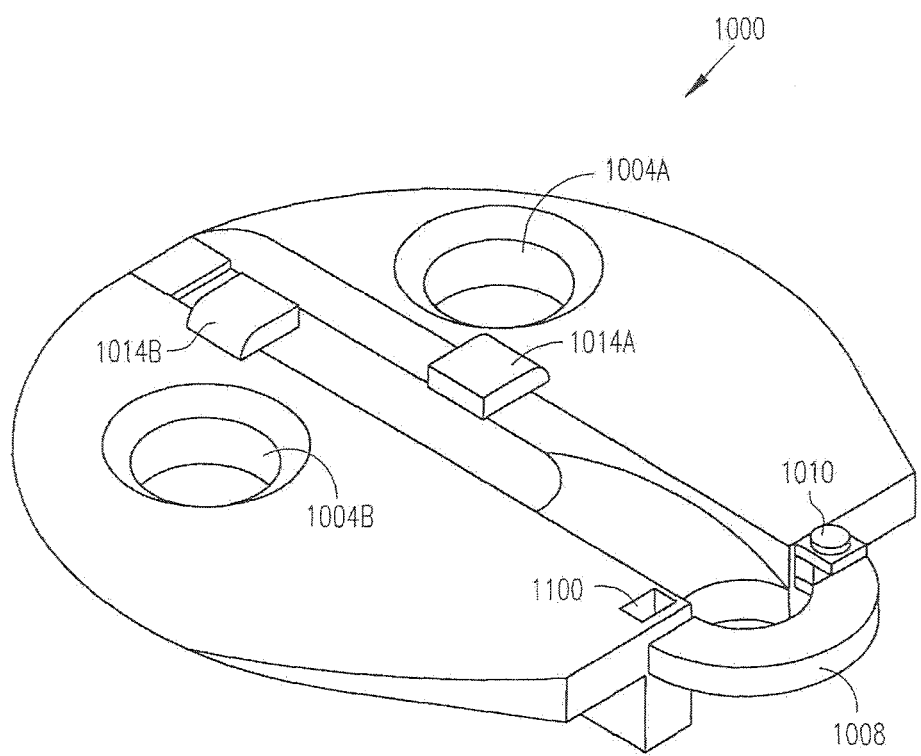
FIG. 12 is a perspective view of the third instrument immobilizer with the clasp in its closed position.
Figure 13:
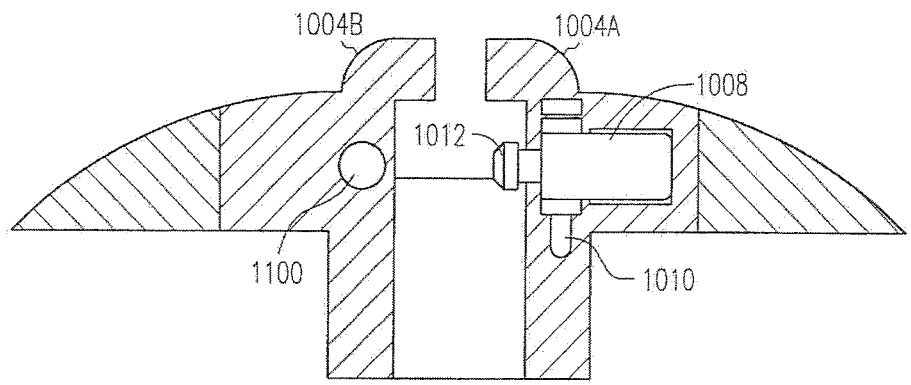
FIG. 13 is a side view of the third instrument immobilizer with the clasp in its open position.
Figure 14:
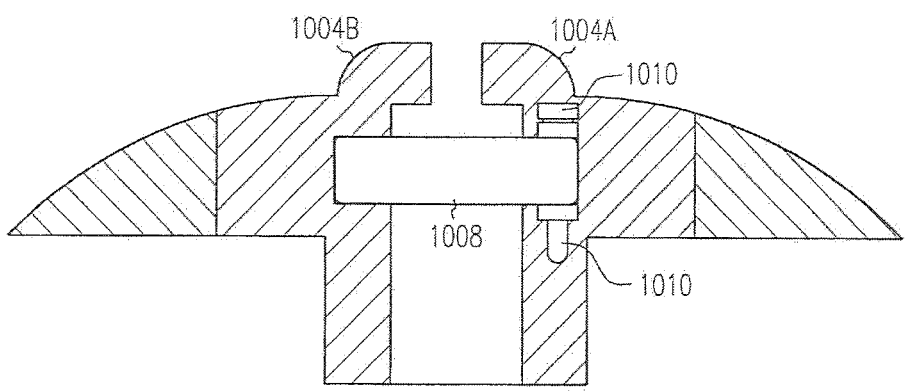
FIG. 14 is a side view of the third instrument immobilizer with the clasp in its closed position.

FIG. 11 is a top view of instrument immobilizer 1000 with clasp 1008 in the closed position. FIG. 12 is a perspective view of instrument immobilizer 1000 with clasp 1008 in its closed position. FIG. 13 is a side view of instrument immobilizer 1000 with clasp 1008 in its open position. FIG. 14 is a side view of instrument immobilizer 1000 with clasp 1008 in its closed position.

Figure 24:
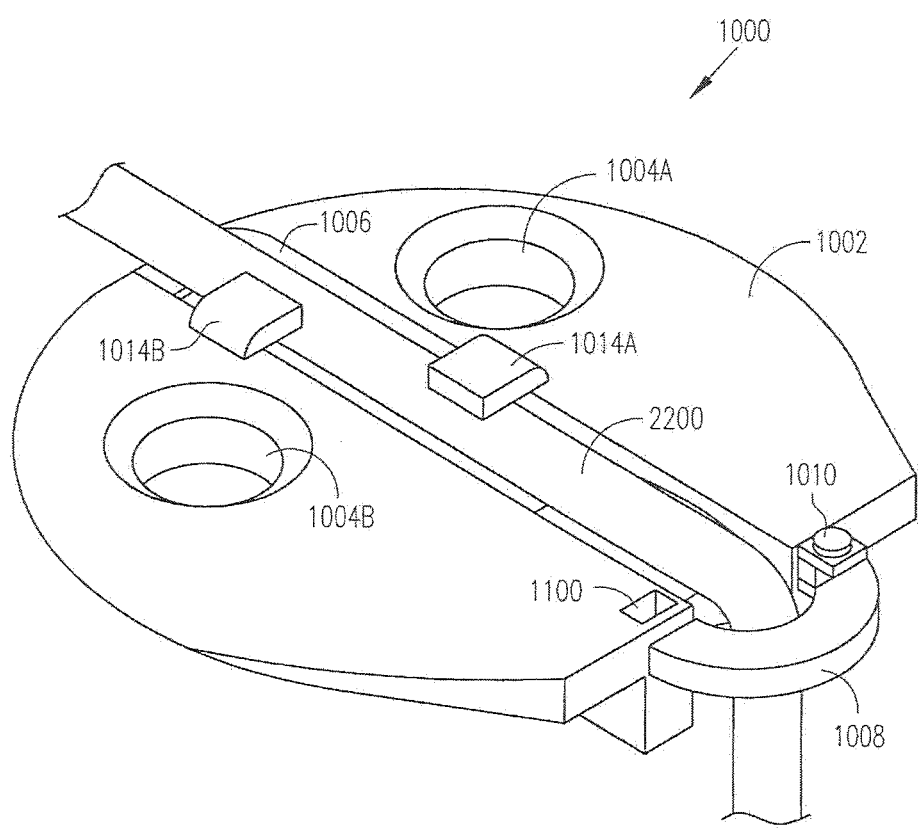
FIG. 24 is a perspective view of the third instrument immobilizer with the clasp in the closed position where the clasp immobilizes an instrument.

FIG. 24 is a perspective view of an instrument immobilizer retaining a wire electrode or other instrument 2200 (for example, a catheter for aspiration or substance infusion). The instrument immobilizer base 1002 is secured to the skull such that clasp 1008 is cantilevered over the burr hole or other entry portal. The electrode or other instrument is inserted through the burr hole or other entry portal to the desired location so the instrument is near the clasp 1008. In one option, the instrument is adjacent a side surface of the instrument immobilizer 1000. The clasp 1008 is then closed around the electrode or other instrument to snugly retain it. The electrode or other instrument is laterally bent into lateral groove 1006 and positioned snugly under cantilevered retaining members 1014A-B extending from semicircular portions 1002A-B over lateral groove 1006. As shown in FIG. 24, The electrode or other instrument is thereby immobilized by clasp 1008. Cantilevered retaining members 1014A-B and/or lateral groove 1006 are sized or otherwise configured to snugly conform to the electrode or other instrument. This provides additional snug retention of the electrode or other instrument.

Figure 15:
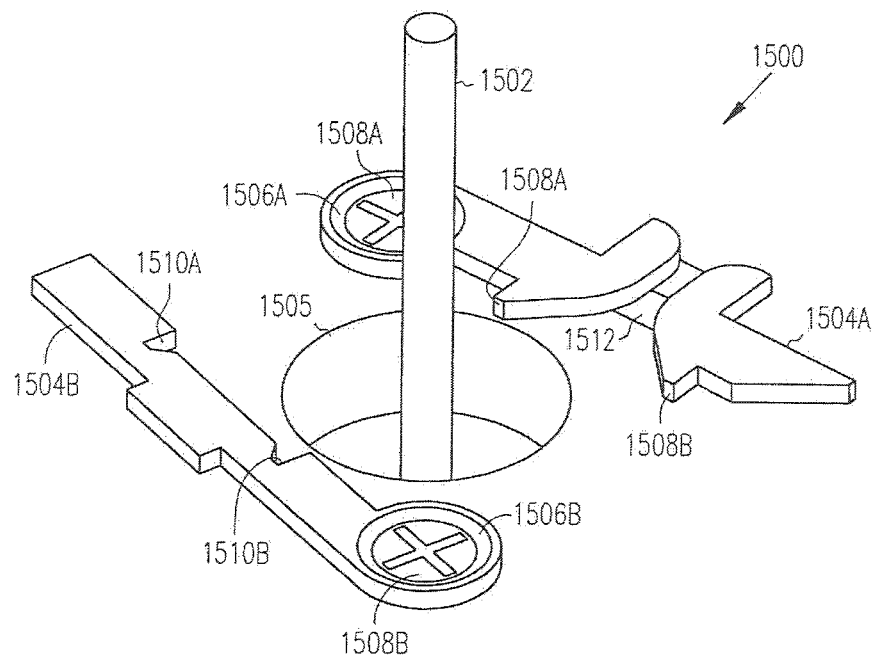
FIG. 15 is a perspective view of a fourth instrument immobilizer with base pieces in an open position.
Figure 16:
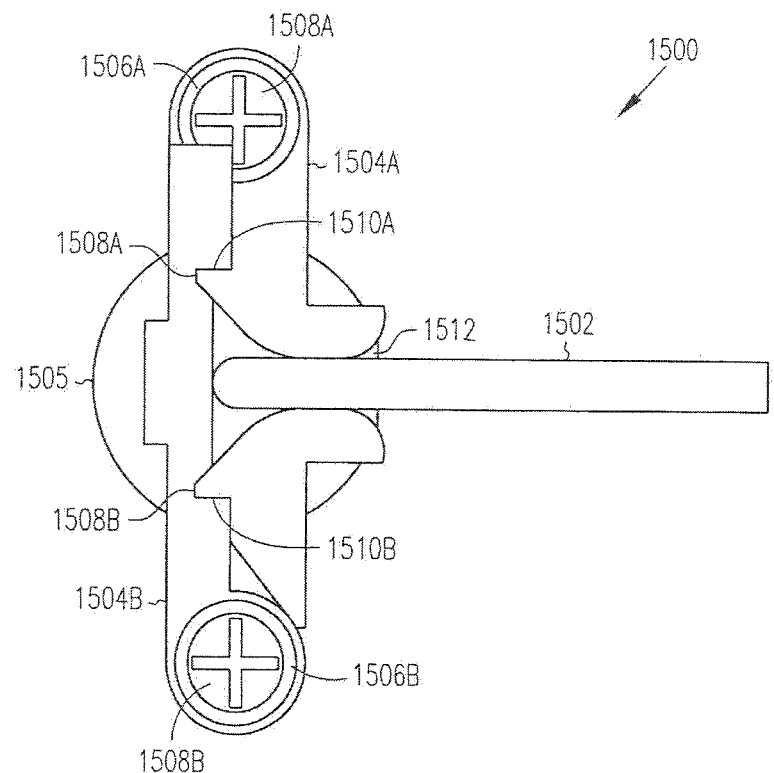
FIG. 16 is a top view of the fourth instrument immobilizer with base pieces in a closed position, grasping and immobilizing a laterally bent electrode.

FIGS. 15-16 illustrate various views of a fourth embodiment of a low-profile instrument immobilizer for securing a flexible recording or stimulating electrode or the like, or other instrument (a catheter, in one example), after it has been introduced through a burr hole or other entry portal to a desired target location in the brain.

FIG. 15 is a perspective view illustrating generally, by way of example, but not by way of limitation, portions of instrument immobilizer 1500 for securing an electrode 1502 or other instrument. In this example, instrument immobilizer 1500 includes a two-piece base 1504A-B. Base piece 1504A is sized and shaped for being disposed along a first side of a burr hole 1505 or other entry portal. Base piece 1504B is sized and shaped for being disposed along a second side of a burr hole or other entry portal. Each elongated base piece 1504A-B includes a corresponding hole 1506A-B, at a first end, for receiving a corresponding bone screw 1508A-B or the like therethrough for securing the corresponding base piece 1504A-B to the subject's skull. In one example, the bone screws 1508A-B and holes 1506A-B are disposed on opposite sides of the burr hole 1505. In another example, the base pieces 1504A-B are sized and shaped so bone screws 1508A-B and holes 1506A-B are disposed at non-opposed locations around the burr hole 1505. Each bone screw 1508A-B and corresponding hole 1506A-B provides a hinge about which the corresponding elongate base piece 1504A-B rotates, such as from the open position illustrated in FIG. 15 to a closed position, in which base pieces 1504A-B retain and immobilize the electrode or other instrument. In one option, the base pieces 1504A-B rotate about parallel axes. In another option the base pieces 1504A-B rotate within the same plane. FIG. 16 is a top view illustrating base pieces 1504A-B in a closed position, retaining and immobilizing a laterally bent electrode 1502.

In the example of FIGS. 15-16, base pieces 1504A-B are disposed such that when these pieces are rotated into the closed position of FIG. 16, male couplers 1508A-B (for example snap fittings) on base piece 1504A engage corresponding mating couplers 1510A-B on base piece 1504B. This fastens base pieces 1504A-B together to retain electrode 1502 therebetween. Electrode 1502 is further laterally bent into the groove 1512 of base piece 1504A. Groove 1512 is sized and shaped to snugly grasp electrode 1502 therein to further retain and immobilize electrode 1502.

Figure 17:
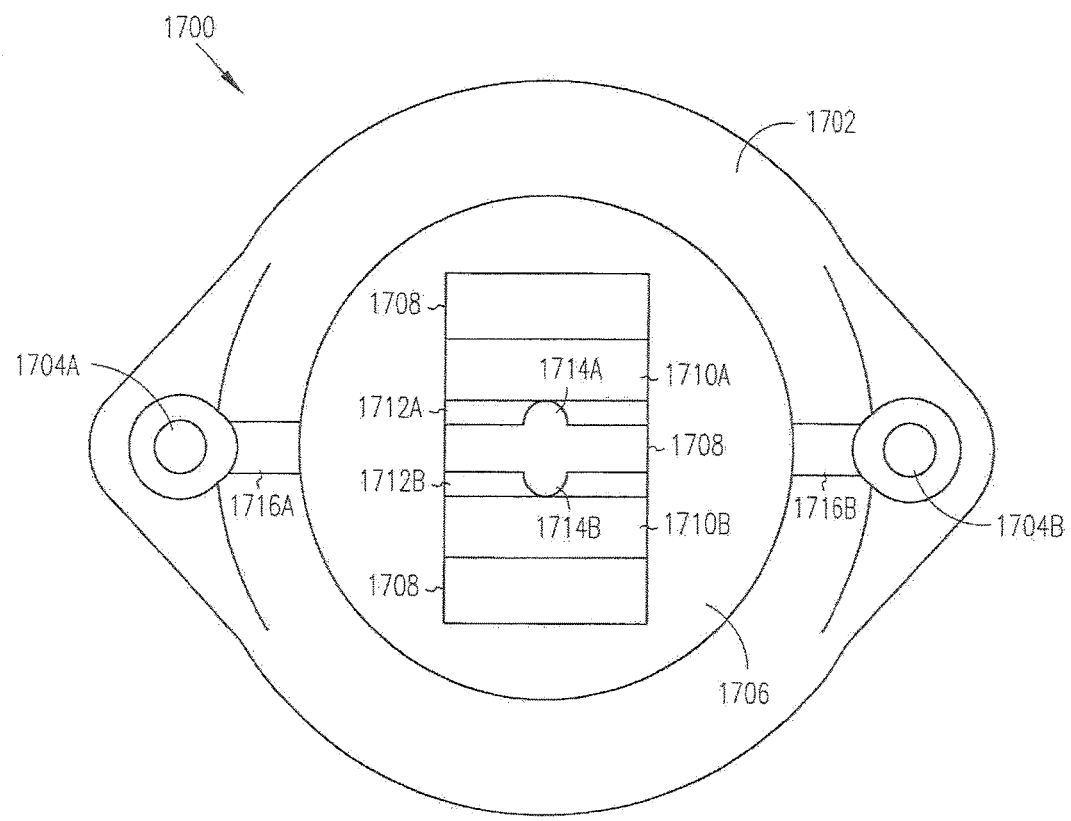
FIG. 17 is a top view of a fifth instrument immobilizer.

FIG. 17 is a top view illustrating generally, by way of example, but not by way of limitation, a fifth embodiment of an instrument immobilizer, such as instrument immobilizer 1700. In this example, instrument immobilizer 1700 includes a hoop-like base 1702 (also referred to herein as a "hoop") sized and shaped for being circumferentially disposed about a burr hole or other entry portal of a desired size. In this example, hoop 1702 includes holes 1704A-B or other passages for receiving corresponding bone screws or the like therethrough for securing hoop 1702 to a subject's skull (or other desired location upon the subject). In this example, hole 1704A is located on an opposite side of hoop 1702 from hole 1704B.

In this example, hoop 1702 defines a center passage therewithin, into which an insert 1706 is disposed. Insert 1706 includes at least one snap-fitting feature that allows insert 1706 to be snapped into hoop 1702. In one example, insert 1706 is inserted into the circular center passage of hoop 1702 such that insert 1706 rotates therewithin with respect to hoop 1702. In this example, the insert 1706 includes at least one detent disposed about the insert bottom surface and projecting to the side of the insert. The hoop 1702 includes a corresponding grooved surface disposed upon an intermediate surface therein. The at least one detent engages the grooved surface. This engagement prevents unwanted rotation of the insert 1706 with respect to the hoop 1702.

In FIG. 17, insert 1706 includes a rectangular or other access opening 1708. Retaining members 1710A-B are movably coupled to the insert 1706. In one example, the retaining members 1710A-B, include slidable retaining members carried substantially within access opening 1708. In one example, access opening 1708 includes opposing side slide rails that allow retaining members 1710A-B to slide toward and away from each other within access opening 1708. In the example of FIG. 17, sliding retaining members 1710A-B each have beveled edges 1712A-B and semicircular cutouts 1714A-B in center portions of beveled edges 1712A-B. When retaining members 1710A-B are positioned adjacent to each other, beveled edges 1712A-B form a lateral groove, and semicircular cutouts 1714A-B are aligned to each other to form a circular opening. In an alternative example, however, the semicircular cutouts 1714A-B are omitted.

In one example, retaining members 1710A-B include respective mating couplings to hold the retaining members in engagement with each other. In one option, the mating couplings include snap-fit features to maintain engagement between the retaining members 1710A-B. In another example, at least one of the retaining members 1710A-B includes an engagement coupling that secures the at least one of the retaining members 1710A-B relative to insert 1706. In one option, the engagement coupling includes a "one-way" toothed surface disposed substantially upon the side slide rails of the insert 1706. Corresponding tabs are disposed along the bottom edge of the at least one of the retaining members 1710A-B. The tabs engage the toothed surface and thereby allow slidable movement of the at least one of the retaining members 1710A-B in one direction, typically toward the other retaining member. In another option, both retaining members 1710A-B have tabs that engage toothed surfaces on the rails. When retaining members 1710A-B contact each other, the tabs engaging the toothed rails maintain engagement between the retaining members 1710A-B. The retaining members 1710A-B do not disengage from each other because the tabs and teeth prevent sliding away in the other direction. If it is desirable to move the retaining members 1710A-B in a direction counter to that allowed by the tabs and teeth the retaining members 1710A-B are pulled out of engagement with the side rails, disengaged from each other and repositioned within the side slide rails.

Figure 18:
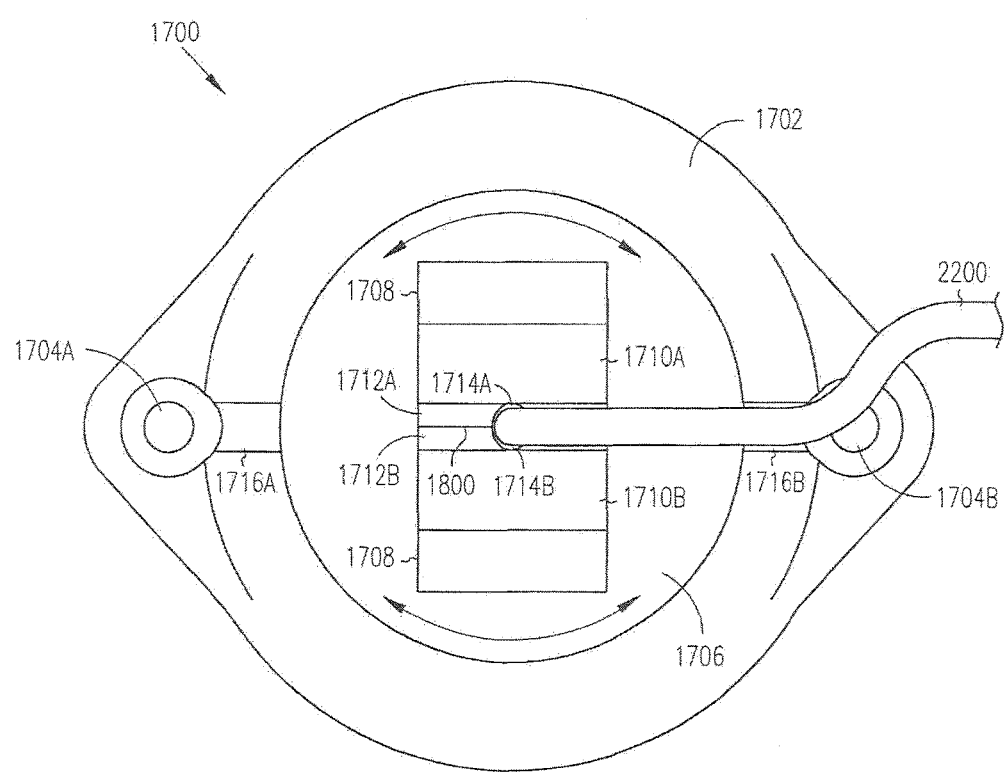
FIG. 18 is a top view illustrating the fifth instrument immobilizer where the first retaining member and second retaining member immobilize an instrument.

FIG. 18 is a top view illustrating instrument immobilizer 1700 retaining a wire electrode or other instrument 2200. In operation, hoop 1702 is secured and insert 1706 is inserted therein. An electrode or other instrument 2200 (for example an aspiration or infusion catheter) is inserted between retaining members 1710A-B to the desired location in the patient's brain. In one example, the insert 1706 is capable of being rotated about the instrument 2200. This provides added flexibility in the location for immobilization of the instrument. Retaining members 1710A-B are moved against each other to snugly retain and immobilize a portion of the instrument 2200, such as within the circular opening defined by semicircular cutouts 1714A-B. In another example, the semicircular cutouts 1714A-B are omitted and the instrument 2200 is compressibly retained between the beveled edges 1712A-B at a desired position anywhere along the beveled edges. The retaining members 1710A-B engage each other and/or the side rails (as discussed above) to immobilize the instrument 2200. If desired, the instrument 2200 can be bent into the lateral groove formed 1800 by beveled edges 1712A-B. In one example, the lateral groove 1800 aligns with one or more lateral exit grooves 1716A-B providing lateral access through hoop 1702, allowing the electrode or other instrument to laterally exit hoop 1702. In one example, the lateral groove 1800 and/or the lateral exit groove(s) 1716A-B are sized and shaped to snugly grasp and retain the instrument 2200. In another example, once the instrument 2200 is immobilized by the retaining member 1710A-B and grasped and retained by the lateral groove 1800 and/or lateral exit groove 1716A-B, a cap is affixed to the instrument immobilizer 1700.

Figure 19:
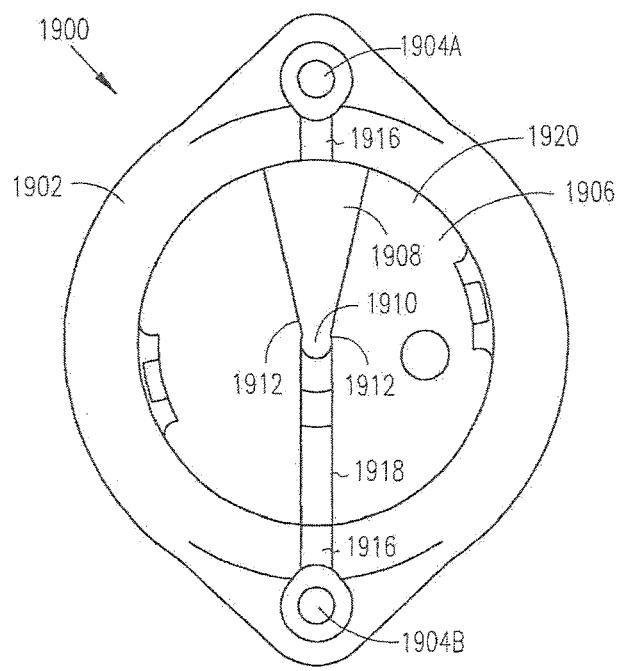
FIG. 19 is a top view of a sixth instrument immobilizer.

FIG. 19 is a top view illustrating generally, by way of example, but not by way of limitation a sixth embodiment of an instrument immobilizer, such as instrument immobilizer 1900. In this example, instrument immobilizer 1900 includes a hoop-like base 1902 (also referred to herein as a "hoop") sized and shaped for being circumferentially disposed about a burr hole or other entry portal of a desired size. In this example, hoop 1902 includes holes 1904A-B or other passages for receiving corresponding bone screws or the like therethrough for securing hoop 1902 to a subject's skull (or other desired location upon the subject). In this example, hole 1904A is located on an opposite side of hoop 1902 from hole 1904B.

In this example, hoop 1902 defines a center passage therewithin, into which a lid 1906 is disposed. Lid 1906 includes at least one snap-fitting feature that allows lid 1906 to be snapped into hoop 1902. In one example, lid 1906 rotates substantially within the circular center passage of hoop 1902. In another example, the lid 1906 includes at least one detent on its bottom surface, and the hoop 1902 includes a corresponding groove on or near its inner periphery. The at least one detent engages the groove. This prevents undesirable rotation of the lid 1906 with respect to the hoop 1902.

In this example, the lid 1906 includes a slot 1908. In one option, the slot 1908 has an arcuate geometry defined by the lid 1906 and extends across an angle of approximately 15 degrees. The slot 1908 extends from an outer edge 1920 of the lid 1906, tapering inward toward a center 1922 of the lid 1906. The slot includes at least one socket 1910. FIG. 19 illustrates the socket 1910 extending through the center of the lid 1906. However, the socket 1910 may alternatively be offset from the center of the lid 1906 to provide added flexibility in positioning and immobilizing an instrument. In one example, the slot 1908 narrows as it extends from the outer edge 1920 of the lid 1906 toward the socket 1910. In FIG. 19, just before reaching the socket 1910, the slot 1908 is slightly more narrow than the socket 1910 is wide. This provides a lip 1912 on the slot 1908 adjacent the socket 1910.

Figure 20:
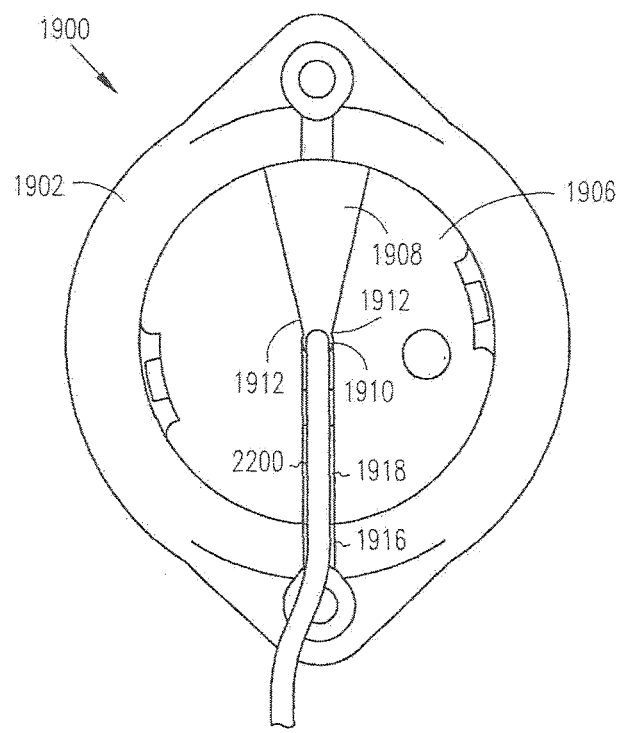
FIG. 20 is a top view illustrating the sixth instrument immobilizer where the socket slot and socket immobilize an instrument.

FIG. 20 is a top view illustrating a wire electrode or other instrument 2200 (e.g., a catheter, such as for aspiration or infusion of drug(s), cell(s) or other substances) that is immobilized by the instrument immobilizer 1900. In one example of operation, hoop 1902 is first secured. The instrument 2200 is then inserted through the hoop 1902 to the desired location in the patient's brain. In one example, the lid 1906 is then inserted into the hoop 1902 such that the instrument 2200 is disposed within a slot 1908. Inserting the lid 1906 after positioning the instrument 2200 provides additional flexibility for positioning the slot around the instrument 2200 so as to reduce or minimize any unwanted movement of the instrument 2200. The instrument 2200 is then advanced laterally within the slot 1908 toward the socket 1910. Upon reaching the lip 1912, a portion of the instrument 2200 and/or the lip 1912 deforms slightly to permit the instrument 2200 to enter the socket 1910 for retention and immobilization by the socket 1910. In one example, the hoop 1902 includes at least one lateral exit groove 1916 and the lid 1906 includes at least one lateral exit groove 1918. The lid 1906 is positionable to permit groove 1918 to align with one of the lateral exit grooves 1916. A portion of the instrument 2200 is then bent and positioned within the groove 1918 and lateral exit groove 1916 where it is retained snugly therein. This further immobilizes the instrument 2200. In one example, a cap is affixed to the instrument immobilizer 1900.

Figure 21:
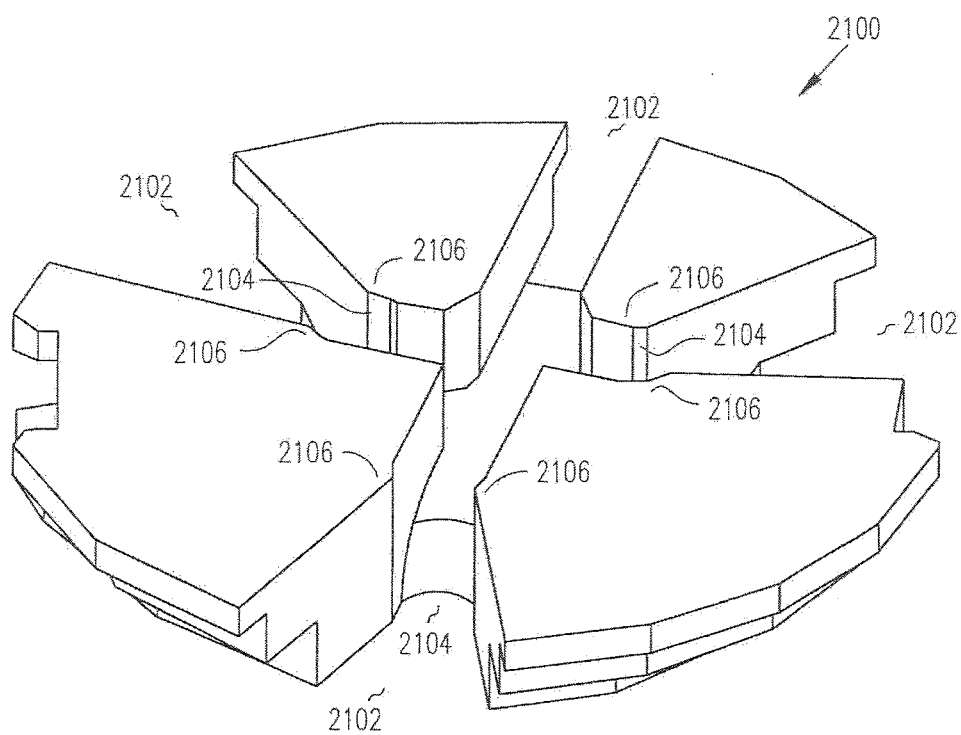
FIG. 21 is a perspective view of another example of the lid for the sixth instrument immobilizer having multiple slots and corresponding sockets.

FIG. 21 is a perspective view of another embodiment of a lid 2100 usable with the instrument immobilizer 1900 illustrating generally multiple slots 2102, sockets 2104 and lips 2106. The lid 2100, as illustrated in the example of FIG. 21, is operable to retain and immobilize up to three instruments. Alternately, the lid 2100 is operable to retain an instrument in multiple positions for flexibility of immobilization. Similar configurations can be used to immobilize fewer or greater instruments.

Figure 25:
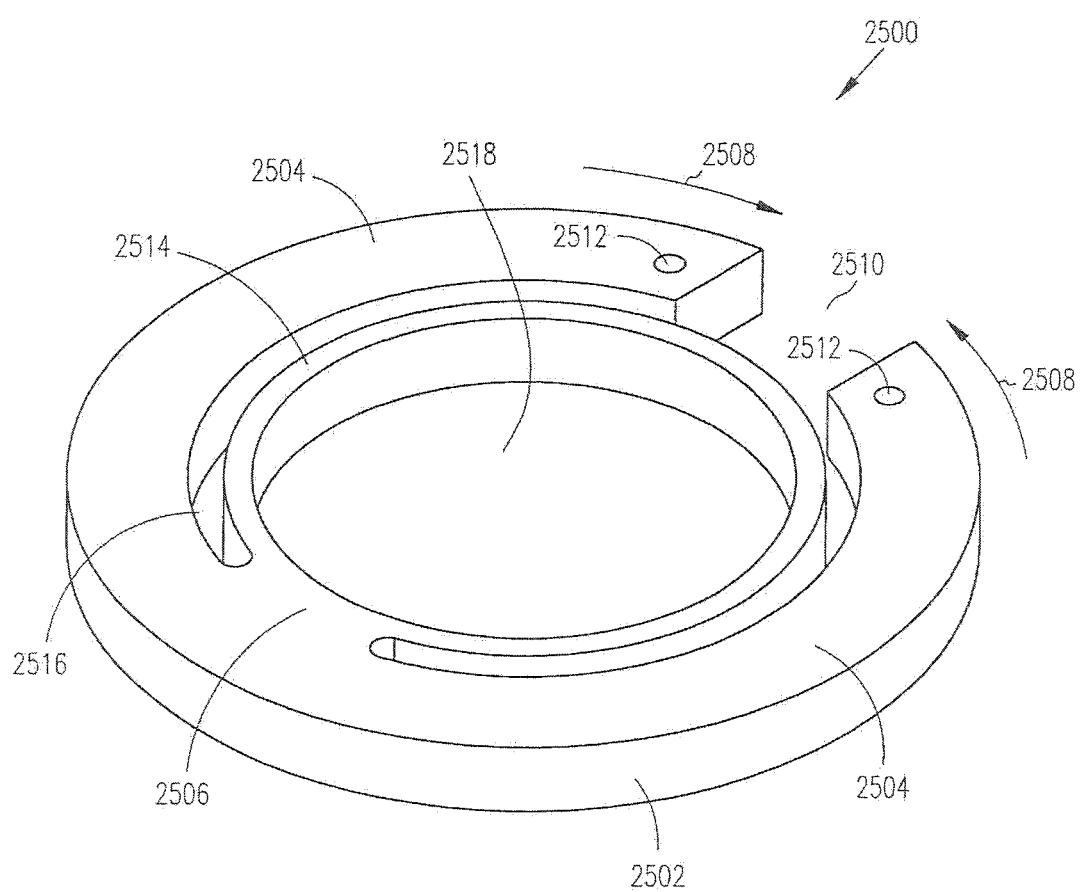
FIG. 25 is a perspective view of an apparatus for positioning an instrument immobilizer within a burr hole.

FIG. 25 is a perspective view illustrating generally, by way of example, but not by way of limitation a seat assembly 2500. In this example, the seat assembly 2500 includes a seat 2502 sized and shaped for being disposed within a burr hole. In one example, the seat has a geometry corresponding to the burr hole, for example a circular shape. In an example, the seat 2502 is constructed from a deformable material having a shape memory property, for example a thermoplastic, which goes by the trade name GRILAMID, and is registered to EMS-Grivory. In another example, the seat 2502 is constructed with polycarbonate. In another example, the seat 2502 includes prongs 2504. The prongs 2504, in one option, are joined substantially adjacent to a bridge 2506. In one example, as shown with arrows 2508, the prongs 2504 are deformable. In another example, the prongs 2504 are pinched and the ends of the prongs 2504 move into the gap 2510. When released, the prongs 2504 expand back toward their original position. In one example, the prongs 2504 are pinched together while inserting the seat assembly 2500 within the burr hole. The prongs 2504 are then released to expand so the outer surfaces of the prongs 2504 engage the inner cylindrical surface defining the burr hole to snugly hold the seat assembly 2500 within the burr hole. In still another example, cavities 2512 are provided in the ends of the prongs 2504. The cavities 2512 allow forceps, or the like, to grasp and pinch the prongs 2504 by inserting the forceps into the cavities 2512.

The seat assembly also includes a collar 2514 coupled to the seat 2502 by the bridge 2506. In one example, the collar 2514 is suspended within the burr hole by the bridge 2506. In other words, the collar 2514 is suspended within a space 2516 defined by the inner surfaces of the seat 2502. In an alternative embodiment, the collar 2514 is disposed above or below the plane defined by the seat 2502. Optionally, where the collar 2514 is disposed below or above the seat 2502 at least the outer surface of the collar 2514 may have a greater circumference than the inner surface of the seat 2502. In another example, the bridge 2506 spans a distance between the seat 2502 and the collar 2514 substantially equal to the distance between the inner surface of the seat 2502 and the outer surface of the collar 2514. In one example, the collar 2514 is spaced from the seat 2502 so where the prongs 2504 are in an undeformed or deformed condition they do not contact the collar 2514. In an example, the collar 2514 defines a socket 2518 and is dimensioned and configured to retain an instrument immobilizer seated therein, for example instrument immobilizer insert 1706. In still another example, the seat assembly 2500 and instrument immobilizer insert 1706 are integral to each other.

Figure 26:
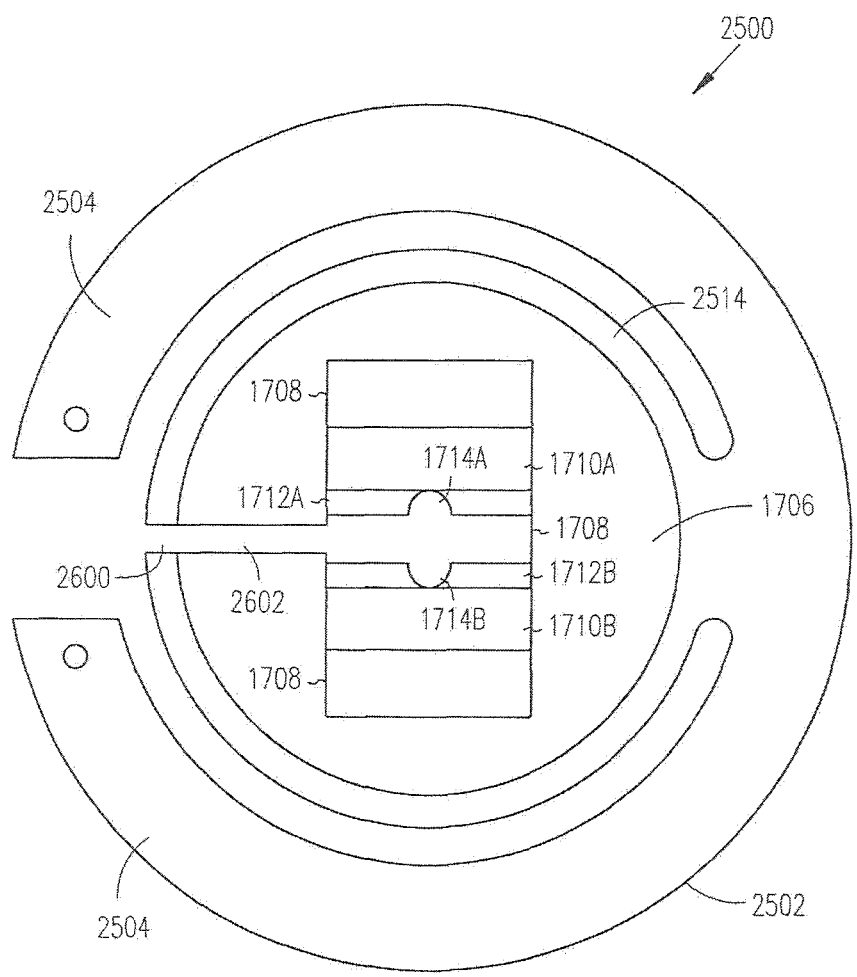
FIG. 26 is a top view of an instrument immobilizer coupled to an apparatus for positioning an instrument immobilizer.

FIG. 26 is a top view showing instrument immobilizer insert 1706 seated within the socket provided by the collar 2514 of the seat assembly 2500. In one example, the collar 2514 includes a slit 2600 sized and shaped to pass an instrument therethrough. The instrument immobilizer insert 1706, in another example, includes a corresponding slit 2602 sized and shaped to pass an instrument between the retaining members 1710A-B. The slit 2602 is aligned with the slit 2600 to permit movement of the instrument from outside the collar 2514 toward the retaining member 1710A, B. Optionally, the collar 2514 is dimensioned and configured to retain a variety of instrument immobilizer inserts, including, but not limited to, inserts configured like instrument immobilizers 100, 600, 1000, 1500, or 1900 and lid 2100. In one option, when using the seat assembly 2500 bone screws are not needed as the instrument immobilizer is snugly retained by the collar 2514 and the seat 2502 is retained within the burr hole by the prongs 2504.

Figure 27:
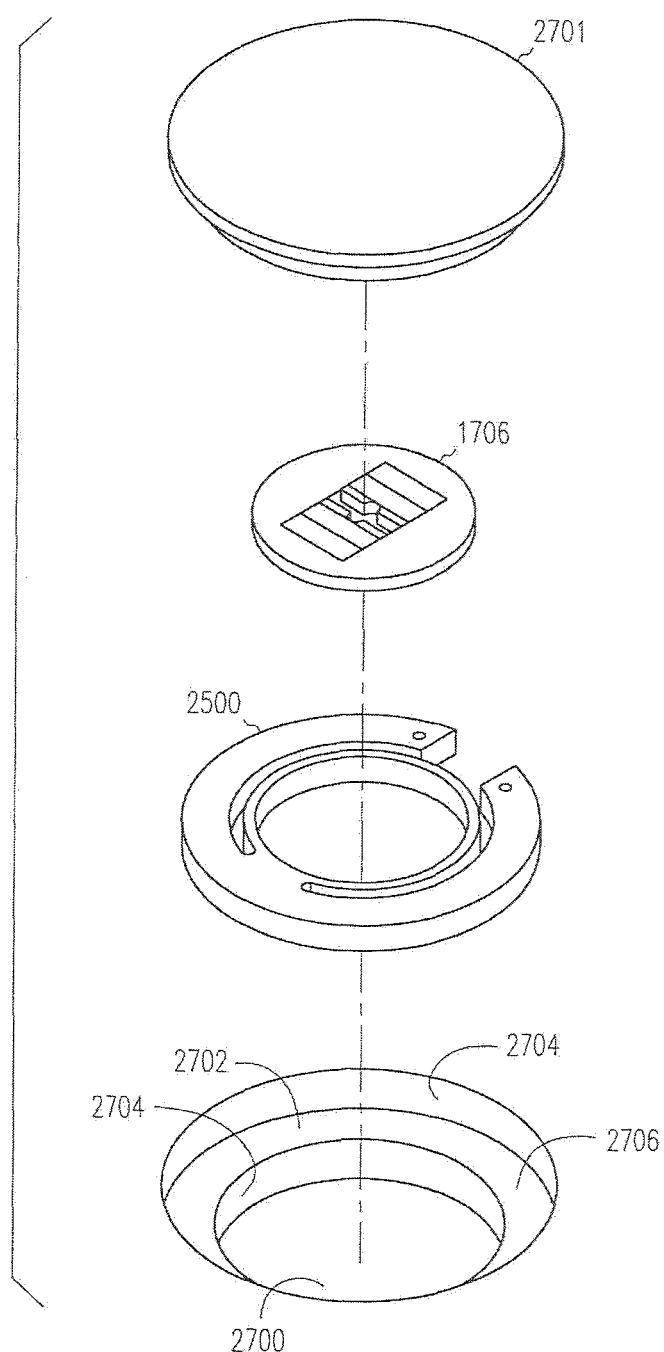
FIG. 27 is an exploded view of an apparatus for positioning an instrument immobilizer, an instrument immobilizer, a cap and a burr hole having including a countersink.

FIG. 27 is an exploded view showing one example of a burr hole 2700, seat assembly 2500, instrument immobilizer insert 1706 and cap 2701. In this example, the burr hole 2700 includes a countersink 2702. At least a portion of the inner surface 2704 of the burr hole 2700 and a shelf 2706 within the burr hole 2700 define the countersink 2702. In one example, the lower surface of the seat 2502 is disposed on the shelf 2706 and the outer surfaces of the prongs 2504 are snugly coupled to the inner surface 2704 of the burr hole 2700. In another example, the cap 2701 is disposed over the instrument immobilizer and snugly coupled to the instrument immobilizer and/or the seat assembly 2500. Optionally, the cap 2701 covers the instrument immobilizer and an instrument immobilized therein and provides a semi-permanent fixture for both. In another option, the cap 2701 is constructed with a biocompatible polymer (e.g. santoprene, polyurethane, silicone or the like). In yet another option, the cap 2701 is constructed with a deformable material so the cap 2701 may be press fit around the seat assembly 2500.

The seat assembly 2500 and the instrument immobilizer insert 1706 optionally include slits 2600, 2602 as shown in FIG. 26 and described above.

Figure 28:
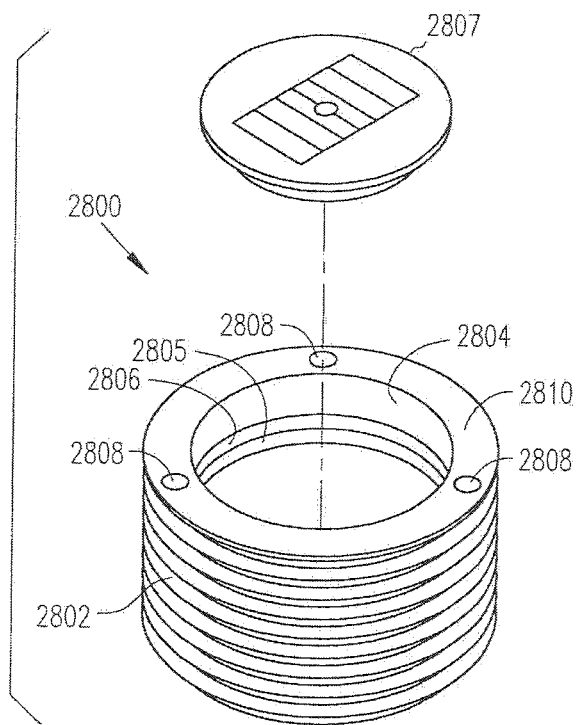
FIG. 28 is a perspective view of another example of an apparatus for positioning an instrument immobilizer within a burr hole.

FIG. 28 is a perspective view of another example of a seat assembly 2800. In one example, the seat assembly 2800 is substantially cylindrical and dimensioned and configured to snugly couple with an inner surface of a burr hole. In one option, the burr hole has a substantially cylindrical geometry corresponding to the seat assembly 2800. In another example, the seat assembly 2800 includes threading 2802 along an outer surface of the seat assembly 2800 for securing the seat assembly 2800 within the burr hole. Optionally, the threading 2802 is self tapping and correspondingly threads the bone surface defining the burr hole as the seat assembly 2800 is inserted in the burr hole. In yet another example, the outer surface of the seat assembly 2800 is smooth and is dimensioned and configured to be press fit into the burr hole.

An inner surface of the seat assembly 2800 defines an access lumen 2804. In one option, the access lumen 2804 is dimensioned and configured so an instrument immobilizer, for example, instrument immobilizer insert 1706 is capable of being disposed within the access lumen 2804. In yet another example, the seat assembly 2800 includes a collar 2806. In one option, the collar 2806 extends from the inner surface of the seat assembly 2800 and forms an annular ridge within the access lumen 2804. In another option, the collar 2806 is a discontinuous flange within the access lumen 2804. The collar 2806 is dimensioned and configured to couple with an instrument immobilizer such as instrument immobilizer insert 1706. In one example, the collar 2806 includes at least one snap fitting 2805 sized and shaped to engage with a corresponding projection, such as snap fitting 2807, on the instrument immobilizer insert 1706 to retain the insert 1706 in the collar 2806. The snap fitting 2805 defines a socket and is sized and shaped to receive the snap fitting 2807. In another example, the collar 2806 is dimensioned and configured to retain a variety of instrument immobilizer inserts, including, but not limited to, inserts configured like instrument immobilizers 100, 600, 1000, 1500, or 1900 and lid 2100.

In one option, when the seat assembly 2800 is inserted within the burr hole the seat assembly 2800 is substantially flush with the surface of the skull or disposed beneath the surface of the skull. In another option, when the instrument immobilizer insert 1706 is coupled to the seat assembly 2800 and the seat assembly 2800 is inserted within the burr hole, the insert 1706 is substantially flush with the surface of the skull or disposed beneath the surface of the skull. Optionally, the seat assembly 2800 and instrument immobilizer insert 1706 present no profile above the surface of the skull when inserted within the burr hole.

In another example, the seat assembly 2800 includes tool cavities 2808. In one option, the multiple tool cavities 2808 are formed in an end surface 2810 of the seat assembly 2800. In another option, the tool cavities 2808 are dimensioned and configured to receive the tines of a driving instrument. Optionally, the driving instrument is used to turn the threaded seat assembly 2800 and screw the seat assembly 2800 into the burr hole.

Figure 29:
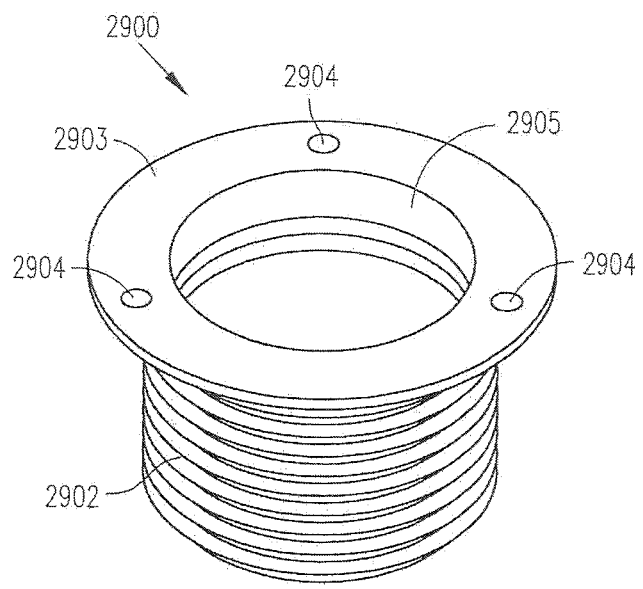
FIG. 29 is a perspective view of yet another example of an apparatus for positioning an instrument immobilizer within a burr hole.

FIG. 29 is a perspective view of yet another example of a seat assembly 2900. In some respects, seat assembly 2900 is similar to seat assembly 2800. In one example, seat assembly 2900 includes threading 2902 similar to seat assembly 2800. In one option, the threading 2902 is self tapping and correspondingly threads the bone surface defining the burr hole as the seat assembly 2800 is inserted in the burr hole. The seat assembly 2900 includes a flange 2903. In one example, the flange 2903 extends radially from an access lumen 2905 and has a sloping geometry to create a smooth profile over the skull when the seat assembly 2900 is disposed within the burr hole. In another example, the flange 2903 is an annular ridge extending around the seat assembly 2900.

In another example, the flange 2903 includes tool cavities 2904. The tool cavities 2904 are dimensioned and configured to receive the tines of a driving instrument. Optionally, the driving instrument is used to turn the threaded seat assembly 2900 and screw the seat assembly 2900 into the burr hole. The flange 2903 serves as a depth stop as the seat assembly 2900 is driven into burr hole. In one option, the flange 2903 positions the seat assembly 2900 at a predetermined depth within the burr hole.

Figure 30:
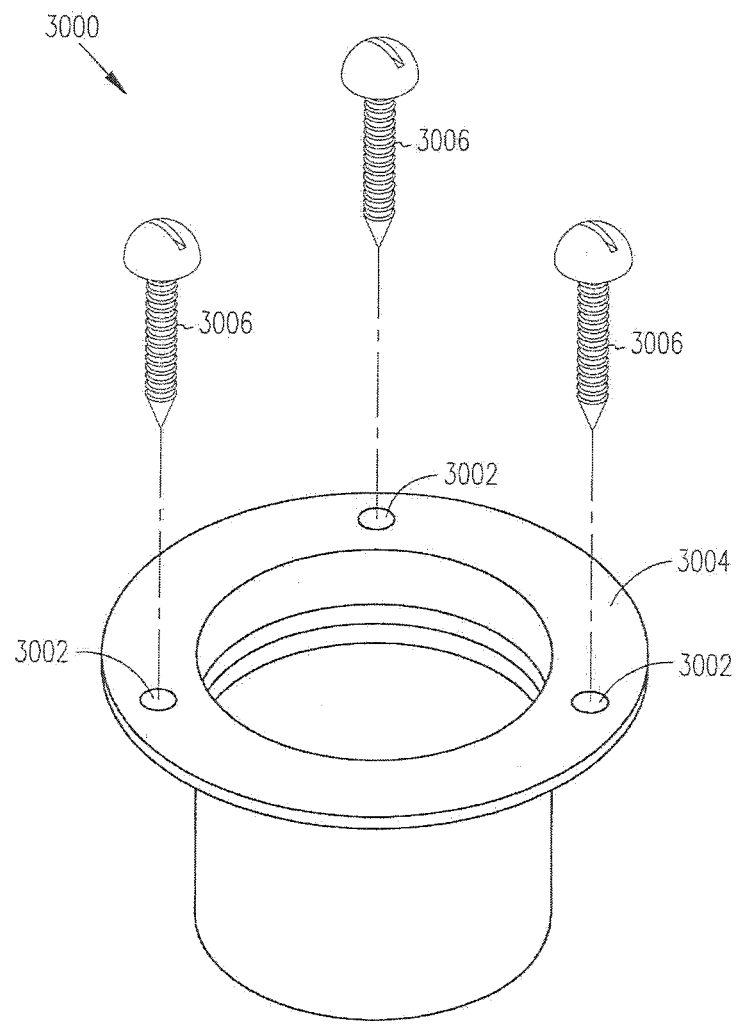
FIG. 30 is an exploded view of still another example of an apparatus for positioning an instrument immobilizer within a burr hole.

FIG. 30 is an exploded view of still another example of a seat assembly 3000. In some respects, seat assembly 3000 is similar to seat assemblies 2800, 2900. Seat assembly 3000 includes tool cavities 3002 that extend through the flange 3004. In another option, the tool cavities 3002 receive fasteners such as screws 3006 or the like that are driven into the skull. The screws 3006 secure the seat assembly 3000 to the skull. The outer surface of the seat assembly 3000 is smooth and is dimensioned and configured to be press fit into a burr hole. The press fit engagement of the seat assembly 3000 temporarily retains the seat assembly 3000 within the burr hole. Optionally, the seat assembly 3100 is then securely coupled to the surface around the burr hole with fasteners, such as screws 3006, described above. Optionally, the outer surface of the seat assembly 3000 includes threading similar to the outer surfaces of the seat assemblies 2800, 2900, described above.

Figure 31A:
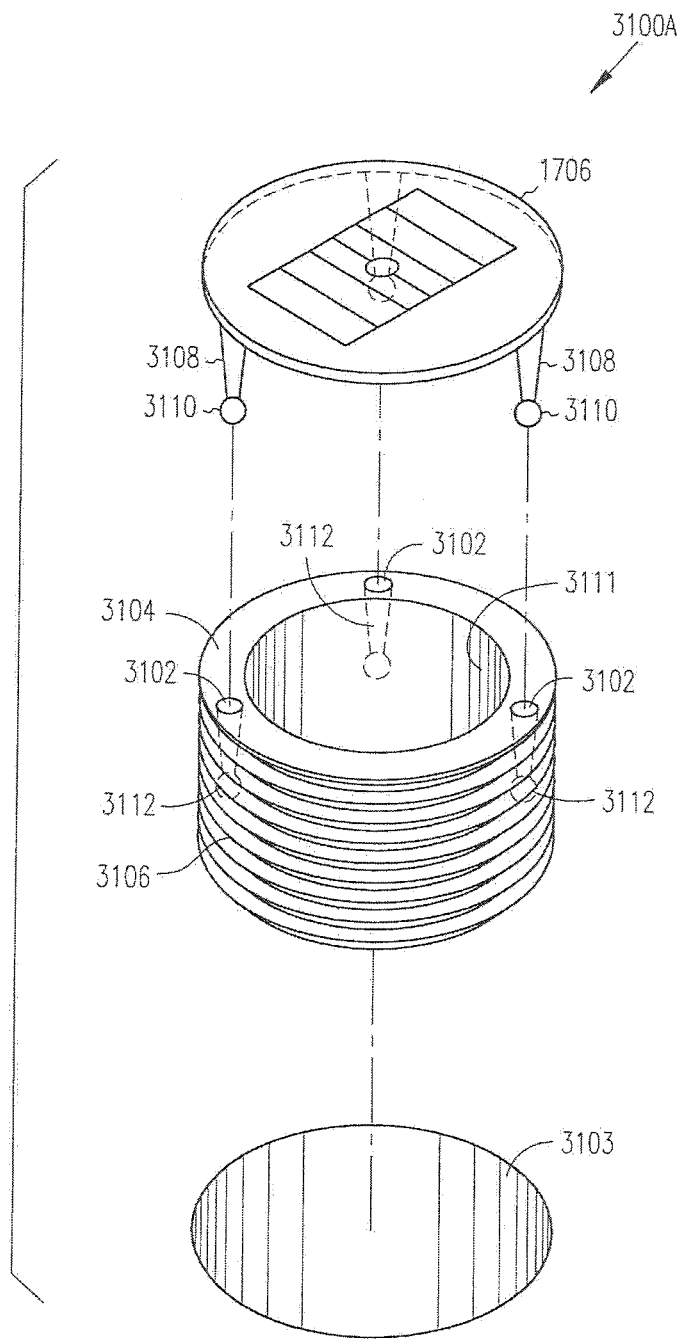
FIG. 31A is an exploded view of an additional example of an apparatus for positioning an instrument immobilizer within a burr hole.

FIG. 31A is an exploded view of another example of a seat assembly 3100A. In one example, the seat assembly 3100A is cylindrical and dimensioned and configured to snugly couple with an inner surface of the burr hole 3103. In another example, the seat assembly 3100A includes threading 3106 along an outer surface for securing the seat assembly 3100A within the burr hole 3103. In yet another example, the outer surface of the seat assembly 3100A is smooth and is dimensioned and configured to be press fit into the burr hole 3103. In still another example, seat assembly 3100A includes tool cavities 3102 in an end surface 3104. As described above with the seat assemblies 2800, 2900, 3000, the tool cavities 3102 are dimensioned and configured to receive the tines of a driving instrument for inserting the seat assembly 3100A within the burr hole 3103.

An inner surface of the seat assembly 3100A defines an access lumen 3111. In one example, an instrument immobilizer, for example, instrument immobilizer insert 1706 is coupled to the seat assembly 3100A and disposed above the access lumen 3111. In one option, the instrument immobilizer insert 1706 has an outer perimeter substantially corresponding to the outer perimeter of the seat assembly 3100A. As a result, the instrument immobilizer insert 1706 has an outer perimeter substantially corresponding to an inner perimeter of the burr hole 3103. Optionally, the instrument immobilizer insert 1706 has a diameter of about 14 millimeters.

Optionally, at least one of the seat assembly 3100 and the insert 1706 includes projections and/or sockets sized and shaped to couple the insert 1706 with the seat assembly 3100 by a snap fit. In one example, the instrument immobilizer insert 1706 includes projections, such as posts 3108, extending from one face of the insert 1706. In one option, the posts 3108 are dimensioned and configured to snugly fit within the tool cavities 3102. In another option, the posts 3108 include snap fittings 3110. In yet another option, the tool cavities 3102 include corresponding sockets 3112 dimensioned and configured to receive the snap fittings 3110. The snap fittings 3110 and sockets 3112 are dimensioned and configured to snugly couple the instrument immobilizer insert 1706 to the seat assembly 3100. In another example, the seat assembly 3100 is dimensioned and configured to snugly couple with a variety of instrument immobilizer inserts, including, but not limited to, inserts configured like instrument immobilizers 100, 600, 1000, 1500, or 1900 and lid 2100.

Figure 31B:
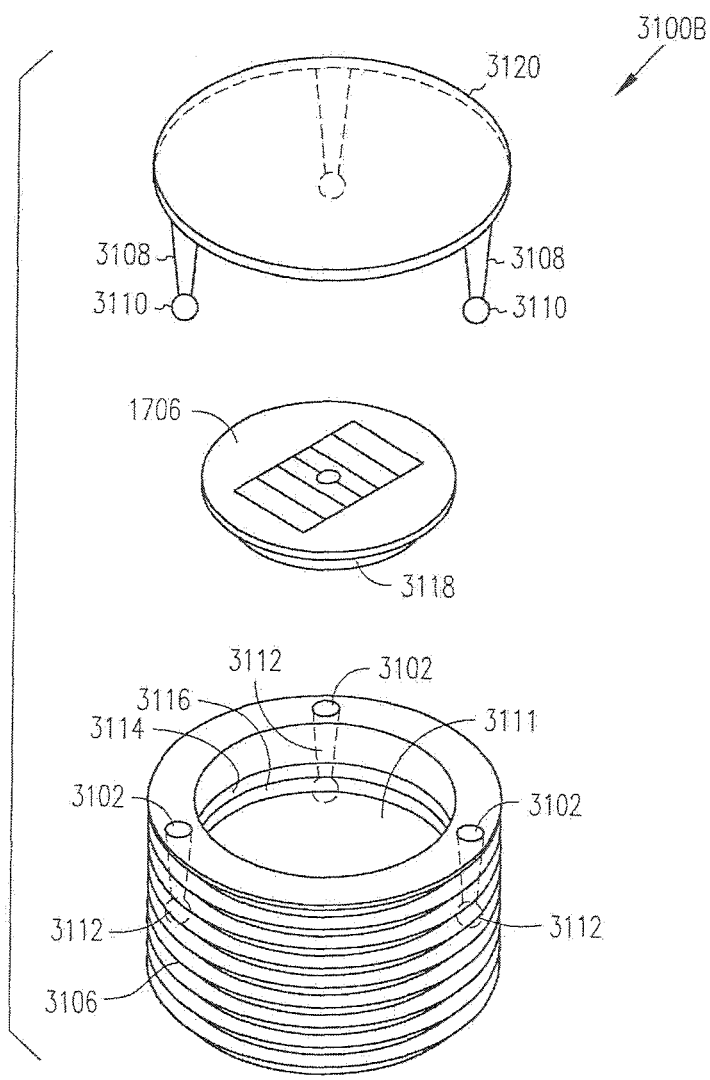
FIG. 31B is an exploded view of a further example of an apparatus for positioning an instrument immobilizer within a burr hole.

FIG. 31B shows another example of a seat assembly 3100B. The instrument immobilizer insert 1706 has a slightly smaller outer perimeter than the outer perimeter of the seat assembly 3100B. The instrument immobilizer insert 1706 is coupled to the inner surface of the seat assembly 3100B that defines the access lumen 3111. In one example, the seat assembly 3100B includes an annular ridge on the inner surface that defines a collar 3114. The collar 3114 includes at least one snap fitting 3116 sized and shaped to engage with a corresponding projection, such as snap fitting 3118, on the instrument immobilizer insert 1706 to retain the insert 1706 in the collar 3114. The snap fitting 3116 defines a socket and is sized and shaped to receive the snap fitting 3118. In another example, the collar 2806 is dimensioned and configured to retain a variety of instrument immobilizer inserts, including, but not limited to, inserts configured like instrument immobilizers 100, 600, 1000, 1500, or 1900 and lid 2100.

In another example, the seat assembly 3100B includes a cap 3120 sized and shaped to cover the instrument immobilizer insert 1706. At least one of the seat assembly 3100B and the cap 3120 includes projections and/or sockets sized and shaped to couple the cap 3120 with the seat assembly 3100B by a snap fit. In one option, the cap 3120 includes projections, such as posts 3108, extending from one face of the cap 3120. In one option, the posts 3108 are dimensioned and configured to snugly fit within tool cavities 3102. In another option, the posts 3108 include snap fittings 3110. In yet another option, the tool cavities 3102 include corresponding sockets 3112 dimensioned and configured to receive the snap fittings 3110. The snap fittings 3110 and sockets 3112 are dimensioned and configured to snugly couple the cap 3120 to the seat assembly 3100B.

Figure 31C:
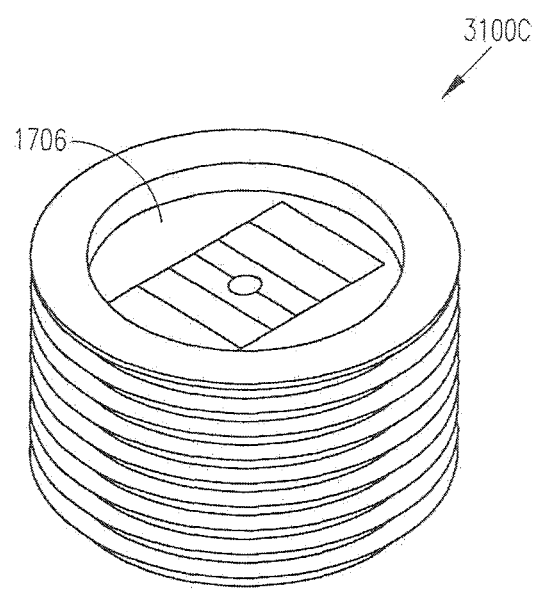
FIG. 31C is an exploded view of a supplementary example of an apparatus for positioning an instrument immobilizer within a burr hole.

FIG. 31C shows another example of a seat assembly 3100C. The seat assembly 3100C has an integral instrument immobilizer such as instrument immobilizer 1706. In one option, the instrument immobilizer 1706 is formed with the rest of the seat assembly 3100C (e.g., by molding, machining and the like). In another option, the instrument immobilizer 1706 is bonded with the seat assembly 3100C with adhesives, welds (e.g., ultrasonic welding) and the like. In yet another example, the seat assembly 3100C includes a variety of integral instrument immobilizers, including, but not limited to, immobilizers configured like instrument immobilizers 100, 600, 1000, 1500, or 1900 and lid 2100. The seat assembly 3100B, in still another example, includes a cap such as cap 3120 (FIG. 31A, B) sized and shaped to cover the instrument immobilizer 1706.

Referring again to FIGS. 31A-C, in one example, when the seat assembly 3100A-C is inserted within the burr hole the seat assembly 3100A-C is substantially flush with the surface of the skull or disposed beneath the surface of the skull. In another option, when the instrument immobilizer insert 1706 is coupled to the seat assembly 3100A, B and the seat assembly 3100A, B and insert 1706 are inserted within the burr hole, the insert 1706 and/or the seat assembly 3100A, B are substantially flush with the surface of the skull or disposed beneath the surface of the skull. Optionally, the seat assembly 3100A-C and instrument immobilizer insert 1706 present no profile above the surface of the skull when inserted within the burr hole.

In the above examples (aspects of which can be combined with each other), the components of instrument immobilizers 100, 600, 1000, 1500, 1700, 1900, lid 2100, and seat assemblies 2500, 2800, 2900, 3000, 3100 may be manufactured from molded plastic and are MRI compatible. The bone screws used for securing the instrument immobilizers may be manufactured from stainless steel. In one example, such bone screws include imaging fiducial markers integral or attachable thereto. Additionally, in other embodiments of the above examples the exit grooves are disposed at various locations (for example, at regular intervals) about the instrument immobilizers 100, 600, 1000, 1500, 1700, and 1900 to provide flexibility in the placement of the instruments when immobilized. Instrument immobilizers 100, 600, 1000, 1500, 1700, 1900, lid 2100, and seat assemblies 2500, 2800, 2900, 3000, 3100 are not limited to use in conjunction with skull burr holes in neurosurgery, but may be secured at other locations of a patient for securing an electrode or other surgical instrument (for example catheters used for aspiration or infusion), or about or within an entry portal in other objects into which an instrument has been introduced, and which requires immobilization. The above examples provide instrument immobilizers that are designed to advantageously provide a low-profile (e.g., small height) above or flush to the patient's skull. By way of example, but not by way of limitation, in one embodiment, instrument immobilizer 100 provides a height of less than about 0.1 inches, instrument immobilizer 600 provides a height of less than about 0.08 inches, instrument immobilizer 1000 provides a height of less than about 0.08 inches, instrument immobilizer 1500 provides a height of less than about 0.065 inches, instrument immobilizer 1700 provides a height of less than about 0.1 inches, instrument immobilizer 1900 and lid 2100 provide a height of less than about 0.1 inches, and seat assemblies 2500, 2800, 3100 and instrument immobilizer 1700 provide a height of 0.0 inches.

Figure 32:
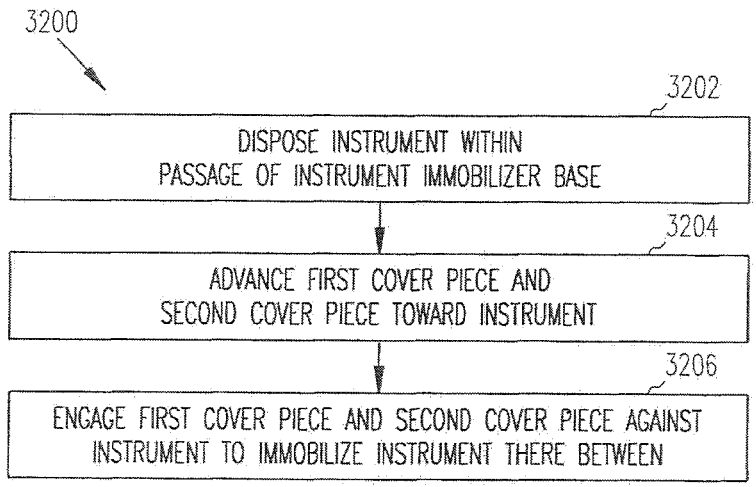
FIG. 32 is a block diagram illustrating generally, by way of example, and not by way of limitation, a first method to immobilize an instrument.

FIG. 32 is a block diagram of a method 3200 for immobilizing an instrument, for example an electrode or catheter. At 3202, an instrument is disposed within a passage of an instrument immobilizer base. At 3204, a first cover piece and a second cover piece are advanced toward the instrument as shown, for example, in FIGS. 1 and 22 with the instrument immobilizer 100 having cover pieces 106A, 106B. At 3206 the first cover piece and the second cover piece are engaged against the instrument to immobilize the instrument therebetween.

Several variations are possible. One example includes sliding the first cover piece through a slot in the instrument immobilizer base and sliding the second cover piece through another slot in the instrument immobilizer base. Another example includes grasping and/or retaining a portion of the instrument within a groove defined by the first and second cover piece.

Figure 33:
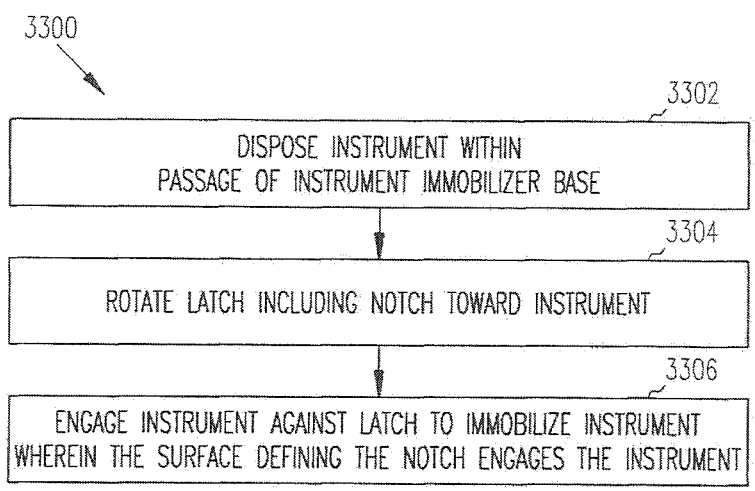
FIG. 33 is a block diagram illustrating generally, by way of example, and not by way of limitation, a second method to immobilize an instrument.

FIG. 33 is a block diagram of a method 3300 for immobilizing an instrument. At 3302, an instrument is disposed within a passage of an instrument immobilizer base. At 3304, a latch including a notch is rotated toward the instrument as shown, for example, in FIGS. 6 and 23 with the instrument immobilizer 600 having the latch 610 and the notch 612. At 3300 the instrument is engaged against the latch to immobilize the instrument, where the surface defining the notch engages the instrument.

Several variations are possible. One example includes retaining the latch against the instrument by engaging a portion of the latch to a mating portion of the instrument immobilizer base. In another example, a portion of the instrument is laterally positioned against the instrument immobilizer base, and the portion of the instrument is tucked under an overlying retaining member that holds the portion of the instrument against the instrument immobilizer base.

Figure 34:
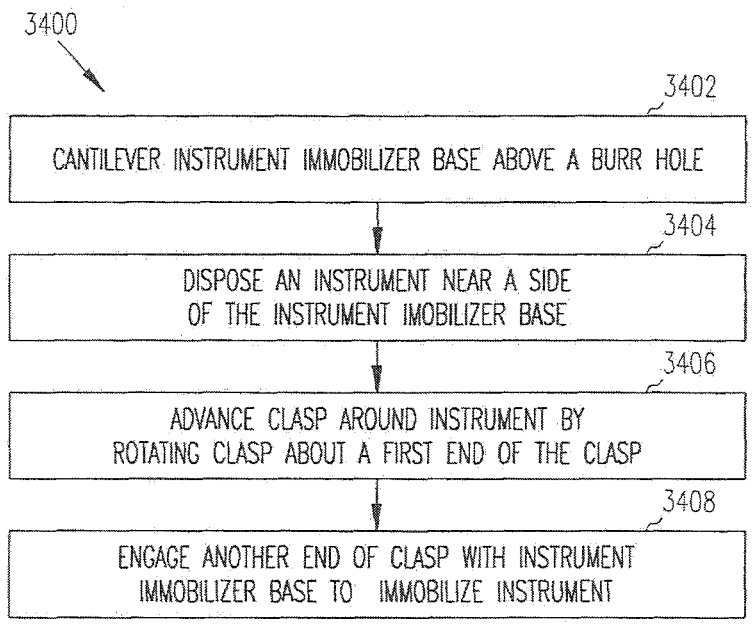
FIG. 34 is a block diagram illustrating generally, by way of example, and not by way of limitation, a third method to immobilize an instrument.

FIG. 34 is a block diagram of a method 3400 for immobilizing an instrument. At 3402, an instrument immobilizer base is cantilevered above a burr hole as shown, for example, in FIGS. 10 and 24 with the instrument immobilizer 1000. At 3404, the instrument is disposed near a side of the instrument immobilizer base. In one example, the instrument is disposed adjacent a side of the instrument immobilizer base. At 3406 the clasp is advanced around the instrument by rotating the clasp about a first end of the clasp. At 3408, another end of the clasp is engaged with the instrument immobilizer base to immobilize the instrument.

Several variations are possible. One example includes positioning a portion of the instrument laterally against the instrument immobilizer base, and tucking the instrument under a retaining member overlying the instrument and a groove. Another example includes snap-fitting the clasp to the instrument immobilizer base.

Figure 35:
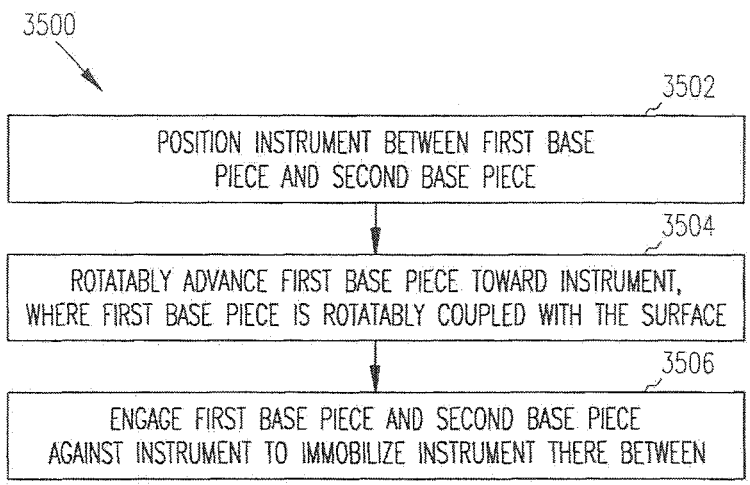
FIG. 35 is a block diagram illustrating generally, by way of example, and not by way of limitation, a fourth method to immobilize an instrument.

FIG. 35 is a block diagram of a method 3500 for immobilizing an instrument. At 3502, an instrument is positioned between a first base piece and a second base piece as shown, for example, in FIGS. 15 and 16 with the instrument immobilizer 1500 having base pieces 1504A, 1504B. At 3504, the first base piece is rotatably advanced toward the instrument. In one example, the first base piece is rotatably coupled to a surface. At 3506, the first base piece and the second base piece are engaged against the instrument to immobilize the instrument therebetween.

Several variations are possible. One example includes rotatably advancing the second base piece toward the instrument, where the second base piece is rotatably coupled with the surface. Another example includes snapping the first base piece together with the second base piece. In still another example, a portion of the instrument is positioned within a groove defined by one of the first base piece or the second base piece.

Figure 36:
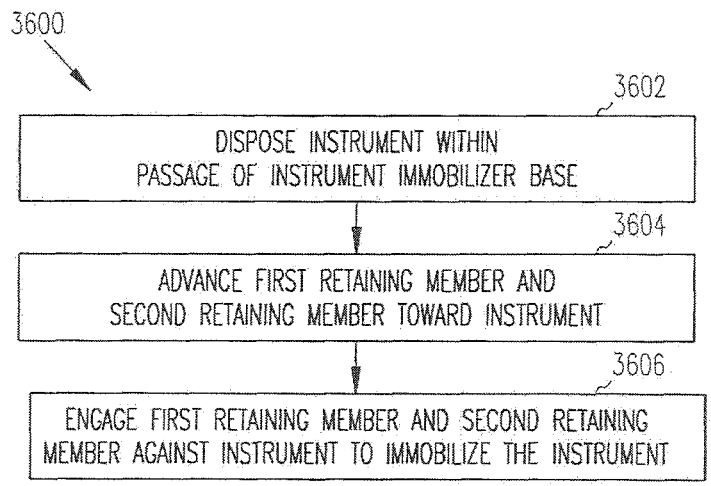
FIG. 36 is a block diagram illustrating generally, by way of example, and not by way of limitation, a fifth method to immobilize an instrument.

FIG. 36 is a block diagram of a method 3600 for immobilizing an instrument. At 3602, an instrument is disposed within a passage of an instrument immobilizer base. At 3604, a first retaining member and a second retaining member are advanced toward the instrument as shown, for example, in FIGS. 17 and 18 with the instrument immobilizer 1700 having the retaining members 1710A, 1710B. At 3606, the first retaining member and second retaining member are engaged against the instrument to immobilize the instrument.

Several variations are possible. One example includes coupling an insert with an instrument immobilizer base. In another example, a portion of the instrument is received along edges of the first and second retaining member.

Figure 37:
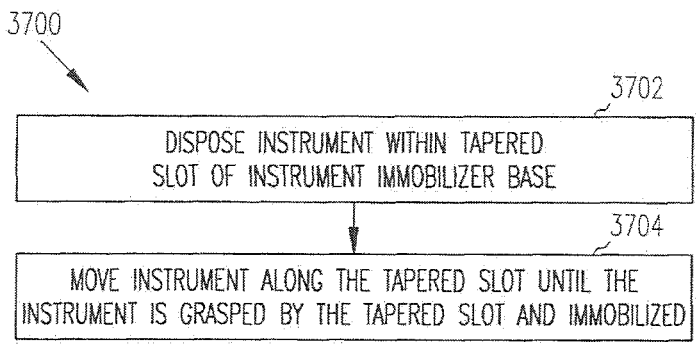
FIG. 37 is a block diagram illustrating generally, by way of example, and not by way of limitation, a sixth method to immobilize an instrument.

FIG. 37 is a block diagram of a method 3700 for immobilizing an instrument. At 3702, an instrument is disposed within a tapered slot of an instrument immobilizer base as shown, for example, in FIGS. 19 and 20 with the instrument immobilizer 1900 having tapered slot 1908. At 3704, the instrument is moved along the tapered slot until the instrument is grasped by the tapered slot and immobilized.

Several variations are possible. One example includes disposing a second instrument within a second tapered slot of the instrument immobilizer base, and moving the second instrument along the second tapered slot until the second instrument is grasped by the second tapered slot and immobilized. In another example, a portion of the instrument is received laterally along the instrument immobilizer base.

Figure 38:
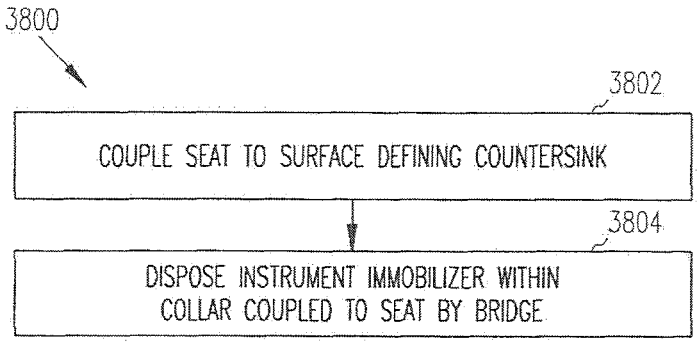
FIG. 38 is a block diagram illustrating generally, by way of example, and not by way of limitation, a first method to position an instrument immobilizer.

FIG. 38 is a block diagram of a method 3800 for positioning an instrument immobilizer. At 3802 a seat is coupled to a surface defining a countersink, such as countersink 2702 shown in FIG. 27. At 3804, the instrument immobilizer is disposed within a collar coupled to the seat by a bridge. One example of a seat and collar is shown in FIG. 25 including the seat 2502 and collar 2514.

Figure 39:
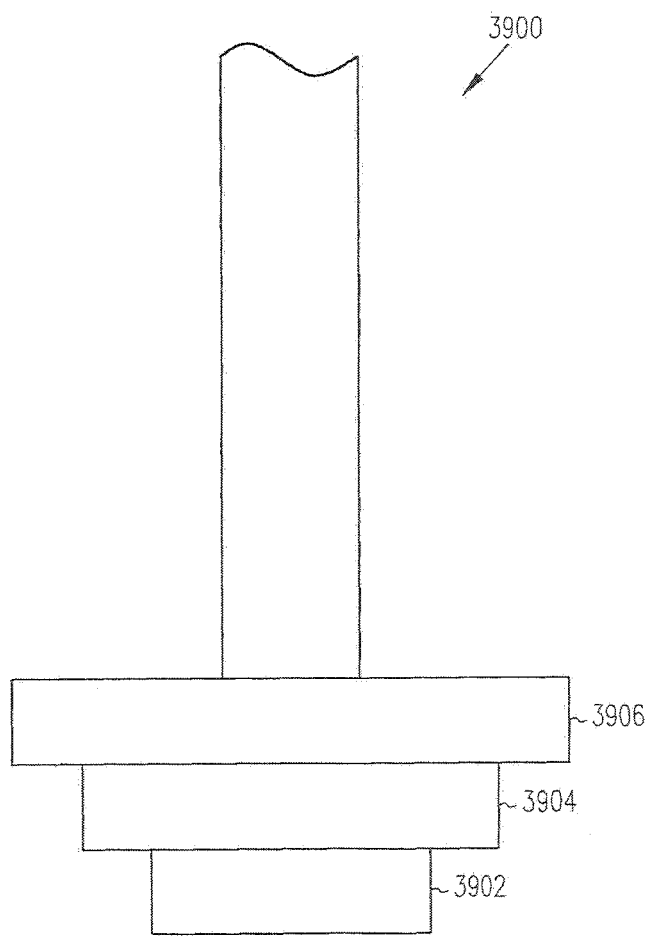
FIG. 39 is a side view of one example of a countersinking drill bit for cutting a countersink into a burr hole.

FIG. 39 is a side view of a countersinking drill bit 3900. In another example, a countersink is cut around the burr hole. Optionally, coupling the seat to the surface defining the burr hole includes coupling the seat to the surface defining the countersink. In one example the countersink is made with the countersinking drill bit 3900 having a central bore 3902 substantially corresponding in size to the burr hole drilled in a skull. The countersinking drill bit 3900 further includes surrounding blades 3904 that extend from the central bore 3902. The central bore 3902 is inserted within the burr hole and the countersinking drill bit 3900 is spun and the surrounding blades 3904 advanced into the skull to define the countersink. In another example, the countersinking drill bit 3900 includes a depth stop flange 3906 above the surrounding blades 3904 to maintain the desired depth of the countersink.

Several variations are possible. One example includes disposing an instrument within a passage of the instrument immobilizer. Another example includes advancing a first cover piece and a second cover piece (e.g. first and second cover pieces 1710A, 1710B) toward the instrument and engaging the first cover piece and the second cover piece against the instrument to immobilize the instrument therebetween. Yet another example includes deforming the seat to fit within the burr hole and releasing the seat so it expands and engages against the surface defining the burr hole. Optionally, deforming the seat is performed without deforming the collar. In another option, disposing the seat within the burr hole is performed prior to disposing the instrument immobilizer within the collar.

Figure 40:
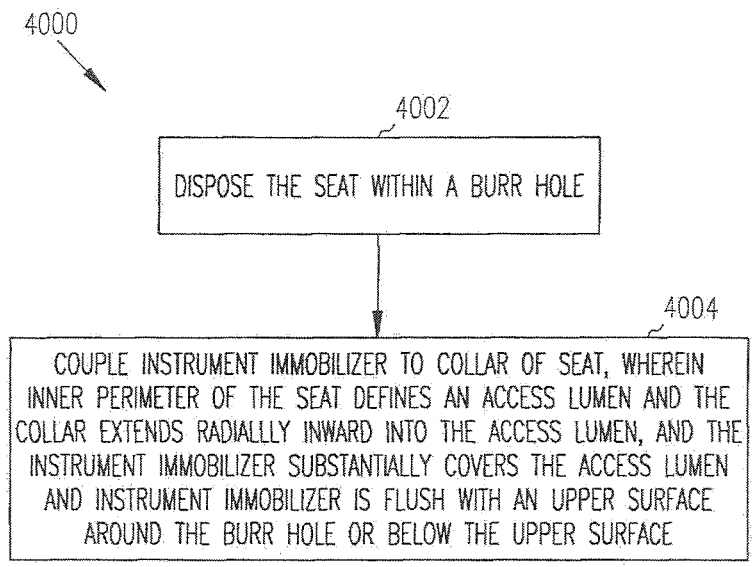
FIG. 40 is a block diagram illustrating generally, by way of example, and not by way of limitation, a second method to position an instrument immobilizer.

FIG. 40 is a block diagram of a method 4000 for positioning an instrument immobilizer. At 4002, a seat is disposed within a burr hole. At 4004, the instrument immobilizer is coupled to a collar of the seat and the instrument immobilizer and/or the seat are flush with an upper surface around the burr hole (e.g. the outer surface of the skull). Optionally, the instrument immobilizer and/or the seat are below the upper surface. In one example, the inner perimeter of the seat defines an access lumen and the collar extends radially inward into the access lumen. In another example, the instrument immobilizer substantially covers the access lumen. One example of a seat and collar is shown in FIG. 28 including the seat 2800 and collar 2806.

Several variations are possible. One example includes snap fitting the instrument immobilizer to the collar. Another example includes screwing the seat into the burr hole. Optionally, the outer perimeter of the seat includes threading. Yet another example includes coupling the instrument immobilizer to the collar of the seat after disposing the seat within the burr hole. Another option includes engaging a flange with an upper surface around the burr hole, wherein the flange extends radially from an outer perimeter of the seat.

Figure 41:
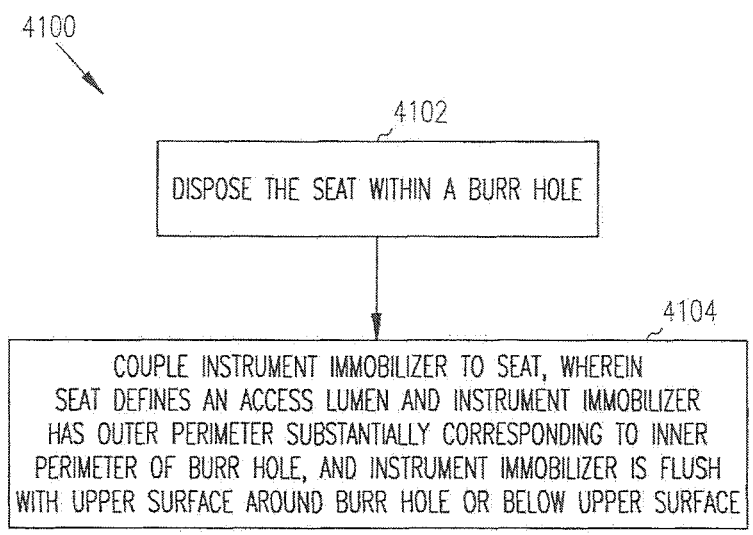
FIG. 41 is a block diagram illustrating generally, by way of example, and not by way of limitation, a third method to position an instrument immobilizer.

FIG. 41 is a block diagram of a method 4100 for positioning an instrument immobilizer. At 4102, a seat is disposed within a burr hole. Examples of seats are shown in FIGS. 31A-C including the seats 3100A-C. At 4104, the instrument immobilizer is coupled to the seat. Optionally, the instrument immobilizer has an outer perimeter substantially corresponding to an inner perimeter of the burr hole. In another example, the seat defines an access lumen. In yet another example, the instrument immobilizer and/or the seat are flush with the upper surface around the burr hole (e.g. the outer surface of the skull). Optionally, the instrument immobilizer and/or the seat are below the upper surface.

Several variations are possible. One example includes snap fitting the instrument immobilizer to an end surface of the seat. Another example includes disposing a post having a snap fitting within a socket dimensioned and configured to receive the snap fitting. Yet another example includes screwing the seat into the burr hole where the outer perimeter of the seat includes threading. Optionally, coupling the instrument immobilizer to the seat is performed after disposing the seat within the burr hole.

Although the above examples have discussed immobilizing an electrode, these examples are also applicable to immobilizing any other instrument, including, but not limited to instruments for surgical, therapeutic, or diagnostic use, including use in non-medical fields where immobilization of an instrument is advantageous. Some examples of such other medical instruments include, by way of example, but not by way of limitation, a catheter (e.g., for aspiration or for infusion of a drug, cells, or another substance), a probe for measuring pressure, temperature, or some other parameter, a biopsy or other needle. Moreover, certain of the above examples that provide a cover for a burr hole or other entry portal may be useful for serving this function as well, even without securing and immobilizing an instrument. Further, in some of the examples above, the instrument immobilizers may be positioned within a burr hole using the seat assembly. Additionally, in other examples, an instrument immobilizer and the seat assembly may be made integral. Furthermore, in the above examples, one or more of such components may be coated, impregnated, or otherwise provided with a drug or other therapeutic agent for delivery to the site at which such component(s) are located. Examples of such agents include steroids or other anti-inflammatory agents, or anti-infection agents such as antibiotics or antiviral drugs.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:
1. An instrument immobilizer apparatus for immobilizing an instrument relative to a patient, comprising:
 a base having an exterior wall defining a central passage, the base sized and shaped to be disposed about a burr hole of a patient; and an insert configured to be disposed within the central passage, the insert defining an access opening through the insert and having a first retaining member with a first edge configured to engage the instrument and a second retaining member with a second edge, wherein the first edge and the second edge are configured to engage the instrument;

wherein the first and second retaining members maintain the first edge opposed to the second edge throughout their full range of movement relative to one another;

wherein the first and second retaining members are configured for holding therebetween the instrument extending through the central passage, the access opening, and into the burr hole;

wherein the insert is configured to be rotated when disposed within the central passage of the base;

wherein the first edge is a first beveled edge;

wherein the second edge is a second beveled edge.

2. The apparatus of claim 1, wherein the base defines a lateral exit groove separate and distinct from the insert;

wherein the instrument extends from the insert and through the exit groove that is sized and shaped to retain a portion of the instrument within the exit groove.

3. The apparatus of claim 2, wherein the base defines first and second holes on opposite sides of the central passage for fastening the base around the burr hole.

4. The apparatus of claim 1, wherein the insert is configured to be selectively coupled to the base with a groove and detent combination to prevent unwanted rotation of the insert relative to the base.

5. The apparatus of claim 1, wherein the insert has an insert wall separate from the base that defines the access opening;

wherein the first retaining member and the second retaining member move relative to the wall.

6. The apparatus of claim 5, wherein the first retaining member and the second retaining member are both movable toward and away from one another within the access opening and relative to the wall.

7. The apparatus of claim 6, wherein the access opening includes opposing side slide rails slidably carrying the first retaining member and the second retaining member.

8. The apparatus of claim 7, wherein the first retaining member and the second retaining member include mating couplings configured to hold the first retaining member and the second retaining member in engagement.

9. The apparatus of claim 8, wherein the mating couplings include snap-fit features.

10. The apparatus of claim 7, wherein at least one of the first retaining member and the second retaining member includes an engagement coupling configured to be secured to the insert, wherein the engagement coupling includes a one-way toothed surface substantially disposed on the slide rails.

11. The apparatus of claim 10, wherein the engagement coupling includes tabs disposed on a bottom surface of the at least one of the first retaining member and the second retaining member, the tabs configured to engage the toothed surface and allow sliding motion of the corresponding one of the first and second retaining members.

12. The apparatus of claim 1, wherein the first and second edges include opposed semicircular surfaces configured to engage the instrument.

13. The apparatus of claim 12, wherein the semi-circular surfaces are configured to form a circular opening when the first retaining member and the second retaining member are positioned adjacent to one another.

14. The apparatus of claim 1, further comprising a cap configured to be affixed to the instrument immobilizer.

15. The apparatus of claim 1, wherein the first beveled edge and the second beveled edge are configured to directly engage the instrument.

16. The apparatus of claim 15, wherein the first beveled edge is configured to be positioned adjacent to the second beveled edge to form a lateral groove.

17. An instrument immobilizer apparatus for immobilizing an instrument relative to a patient, comprising:

a base having a wall defining a central passage, the base being sized and hoop-shaped to be disposed about a burr hole of the patient; and an insert separate from and configured to be disposed within the central passage of the base, the insert having:

a wall that defines an access opening through the insert;

a first retaining member slidably positioned on the wall and within the access opening of the insert and having a first engagement face; and a second retaining member slidably positioned on the wall and within the access opening of the insert and having a second engagement face directed toward the first engagement face;

wherein the first and second engagement faces are configured to be moved relative to another and the wall to engage and hold therebetween the instrument extending through the access opening of the insert and the central passage of the base;

wherein the first and second engagement faces have respective first and second beveled edges.

18. The apparatus of claim 17, wherein the first and second engagement faces include opposed semicircular surfaces configured to engage the instrument.

19. The apparatus of claim 17, wherein the insert is configured to rotate relative to the base prior to the insert being selectively engaged to the base with a groove and detent combination to prevent unwanted rotation of the insert relative to the base.

20. The apparatus of claim 17, wherein the base defines a lateral exit groove sized and shaped to retain a portion of the instrument within the groove.

21. The apparatus of claim 20, wherein the base defines first and second holes on opposite sides of the central passage for fastening the base around the burr hole.

22. The apparatus of claim 17, wherein the first and second retaining members are movable toward and away from one another within the access opening while the first and second engagement faces are directed toward one another.

23. The apparatus of claim 17, further comprising a cap configured to be affixed to the instrument immobilizer.

24. The apparatus of claim 17, wherein the insert is configured to be selectively rotatably positioned within the central passage of the base.

25. The apparatus of claim 17, wherein the insert is configured to be inserted into the central passage of the base and the insert has the access opening formed at least by sides within the insert that allow the first retaining member and the second retaining member to slide within the access opening.

26. The apparatus of claim 17, wherein the first and second retaining members are movable toward and away from one another within the access opening while the first and second engagement faces are directed toward one another;

wherein the first and second engagement faces are moveable relative to one another;

wherein a lateral groove is formed when the first and second beveled edges are adjacent one another.

27. An instrument immobilizer apparatus for immobilizing an instrument relative to a patient, comprising:

a hoop-shaped base having a wall defining a central passage and a grooved surface disposed upon an intermediate surface therein, the hoop-shaped base sized and shaped to be disposed about a cranial burr hole of the patient; and an insert rotatably received within the central passage, the insert having:

a body having an insert wall defining an access opening;

at least one detent disposed about an insert surface and projecting to a side of the body; and a first retaining member and a second retaining member, the first and second retaining members slidable toward and away from one another within the body defining the access opening and relative to the insert wall, the first retaining member having a first engagement face with a first semicircular surface defined in the first engagement face, the second retaining member having a second engagement face with a second semicircular surface defined in the second engagement face, wherein the first and second engagement faces are configured for holding therebetween at the first and second semicircular surfaces the instrument extending through the central passage into the burr hole;

wherein the at least one detent is configured to engage the grooved surface;

wherein the first and second engagement faces have respective first and second beveled edges.

28. The apparatus of claim 27, wherein the first and second retaining members include mating couplings configured to hold the first and second retaining members in engagement.

29. The apparatus of claim 27, wherein the insert is configured to be selectively engaged to the hoop-shaped base with the at least one detent and the grooved surface combination to prevent unwanted rotation of the insert relative to the hoop-shaped base when rotatably received within the central passage.

30. The apparatus of claim 27, wherein the hoop-shaped base defines a lateral exit groove sized and shaped to retain a portion of the instrument within the groove and defines first and second holes on opposite sides of the central passage for fastening the hoop-shaped base around the burr hole.

31. A method of securing a medical instrument on a patient comprising:

mounting a hoop-shaped base around a cranial burr hole at least by passing a fastener through an outer passage, wherein the hoop-shaped base is configured such that a portion of the medical instrument may extend through a central passage of the hoop-shaped base;

moving an insert having an insert wall separate from the hoop-shaped base toward the central passage, the insert further having a first retaining member with a first engagement face and a second retaining member with a second engagement face, wherein the first engagement face is maintained opposed to the second engagement face throughout movement of the first engagement face and the second engagement face;

mounting the insert within the central passage; and moving the first retaining member and second retaining member toward one another and relative to the insert wall to secure the medical instrument through an access opening of the insert;

wherein moving the first and second retaining members toward one another includes sliding at least one of the first or second retaining members relative to the insert wall towards the other of the first or second retaining member;

wherein the first and second engagement faces have respective first and second beveled edges.

32. The method of claim 31, wherein moving the first and second retaining members towards one another further includes moving the first engagement face of the first retaining member toward the second engagement face of the second retaining member, where the first and second engagement faces are directed toward one another throughout movement of the first and second retaining members.

33. The method of claim 32, further comprising capturing the medical instrument between at least a pair of opposed semicircular surfaces in the first and second engagement faces.

34. The method of claim 31, wherein moving the first and second retaining members toward one another includes sliding both of the first and second retaining members toward one another along the insert wall.

35. The method of claim 31, wherein prior to mounting the insert within the central passage, selectively rotatably positioning the insert within the central passage of the hoop-shaped base.

36. The method of claim 31, wherein mounting the insert within the central passage includes snapping the insert within the central passage of the hoop-shaped base.

37. The method of claim 31, wherein moving the first and second retaining members toward one another includes forming a lateral groove by moving the first and second retaining members adjacent one another.

* * * * *